(12) United States Patent
Afar et al.

(10) Patent No.: US 6,277,972 B1
(45) Date of Patent: Aug. 21, 2001

(54) BPC-1: A SECRETED BRAIN-SPECIFIC PROTEIN EXPRESSED AND SECRETED BY PROSTATE AND BLADDER CANCER CELLS

(75) Inventors: Daniel E. Afar, Pacific Palisades; Rene S. Hubert, Los Angeles; Kahan Leong, Playa Del Rey; Arthur B. Raitano; Douglas C. Saffran, both of Los Angeles; Aya Jakobovits, Beverly Hills, all of CA (US)

(73) Assignee: UroGenesys, Inc., Santa Monica, CA (US)

( * ) Notice: Subject to any disclaimer, the term of this patent is extended or adjusted under 35 U.S.C. 154(b) by 0 days.

(21) Appl. No.: 09/374,135

(22) Filed: Aug. 10, 1999

Related U.S. Application Data

(60) Provisional application No. 60/095,982, filed on Aug. 10, 1998.

(51) Int. Cl.[7] ............................ C07H 21/02; C12P 21/06; C12N 15/00; C12N 5/00
(52) U.S. Cl. .................. 536/23.1; 435/69.1; 435/320.1; 435/325
(58) Field of Search ........................ 536/23.1; 435/320.1, 435/69.1, 325

(56) References Cited

FOREIGN PATENT DOCUMENTS

WO 92/01936  2/1992  (WO).
WO 97/39139  10/1997  (WO).

OTHER PUBLICATIONS

Alberts et al., Molecular Biology of the Cell, 3rd edition, 1994, p. 465.*
L. Hillier et al., "The WashU–Merck EST Project," Jul. 16, 1999, XP–002132401, Acc. No. AA013000, 1 pg.
H.O. Sjogren, "Therapeutic immunization against cancer antigens using genetically engineered cells," Immunotechnology 3(1997) 161–172.
R.S. Hubert et al., "Identification of Differentially Expressed Genes Using Prostate Cancer Xenograft Models," The Prostate, Mar. 4, 1999, XP–000877343, 38(4):343.

* cited by examiner

*Primary Examiner*—James O. Wilson
*Assistant Examiner*—Gary B. Nickol
(74) *Attorney, Agent, or Firm*—Gates & Cooper LLP

(57) ABSTRACT

Described is a novel gene and its encoded secreted tumor antigen, termed BPC-1, and to diagnostic and therapeutic methods and compositions useful in the management of various cancers which express BPC-1, particularly including prostate cancer and bladder cancer. In human normal tissues, BPC-1 is only expressed in certain tissues of the brain. However, BPC-1 is expressed at high levels in prostate cancer cells and is also expressed in bladder cancer cells. The structure of BPC-1 includes a signal sequence and a CUB domain. BPC-1 protein is secreted. Preliminary experimental evidence suggests that BPC-1 is directly involved in oncogenesis or maintenance of the transformed phenotype of cancer cells expressing BPC-1. BPC-1 also appears to bind specifically to a cellular protein expressed in prostate cancer cells and other cells.

10 Claims, 17 Drawing Sheets

FIG. 1A

```
          9           18          27          36          45          54
5' CAG CCC CGG GGC GCC GGC CGC GCG CAG CCT CGC TAT CCC ACC CAG GCT CCG GGC
   --- --- --- --- --- --- --- --- --- --- --- --- --- --- --- --- --- ---
          63          72          81          90          99         108
   TTC CAG GAG GGT CGC GGA GCC CCA AGC CAT GAC TAA GGA GCC CAT TTG ATA GCA
   --- --- --- --- --- --- --- --- --- --- --- --- --- --- --- --- --- ---
         117         126         135         144         153         162
   GAG GTG GCG CGC AGC CCG GCG AGC CGA TGA CGG ACC CCT TCT TCC TGC CTT CAA
   --- --- --- --- --- --- --- --- --- --- --- --- --- --- --- --- --- ---
         171         180         189         198         207         216
   TGC CTC AGC GGA AGA TCC CCA AGG GCT GGA GCG AGG AGC GCT GCC GCT GGA CAT
   --- --- --- --- --- --- --- --- --- --- --- --- --- --- --- --- --- ---
         225         234         243         252         261         270
   CCT CCC GGG GAG GCT GCT CCG ACC TGC TGC GCG GCG CGT CTG AGA CTG GGA ACT
   --- --- --- --- --- --- --- --- --- --- --- --- --- --- --- --- --- ---
         279         288         297         306         315         324
   GAG CCA CTC CGC CGC CGC CGG CGC CGC CGC CGC CGC CCG CTC CGT CGC TGC CGT
   --- --- --- --- --- --- --- --- --- --- --- --- --- --- --- --- --- ---
         333         342         351         360         369         378
   CGG TCT GGA CTG GCC CCC ACC TCG CTG CGC CCT CTC CCC GGC CCC GGC CCC GGC
   --- --- --- --- --- --- --- --- --- --- --- --- --- --- --- --- --- ---
         387         396         405         414         423         432
   TCG GGG CGT CCC GGG GCT CGC CCT GCG ACC GCC GCC TCC CGC GCG CCG CGT CCT
   --- --- --- --- --- --- --- --- --- --- --- --- --- --- --- --- --- ---
         441         450         459         468         477         486
   CCC GAC CCC GCG GCG GCG ACG ATG CCC GGG AGG AGG GTC CTG ACG GCG GCG GCG
   --- --- --- --- --- --- --- --- --- --- --- --- --- --- --- --- --- ---
         495         504         513         522         531         540
   CGG ATG GTG GCG GCC GGC GCC GGG GTG TGA TGC GAG CGT CAC GGT GGG GAT GCT
   --- --- --- --- --- --- --- --- --- --- --- --- --- --- --- --- --- ---
         549         558         567         576         585         594
   GCT GGC TGC GCG GCG CTG AGG GCC AGC GAG AGC GAG AGC CCG CCC GGG GCG GAG
   --- --- --- --- --- --- --- --- --- --- --- --- --- --- --- --- --- ---
         603         612         621         630         639         648
   GAC GGA CTC ATC CGG ATC TGG CTG CAG CGT GGG CTC GGA GCT CCC CCT TCC TCT
   --- --- --- --- --- --- --- --- --- --- --- --- --- --- --- --- --- ---
         657         666         675         684         693         702
   CGG TCT CCC TCT CGG CCC CCC TTT ATT TCC TTC TTG CTT TGC GTC TTT AAC ACC
   --- --- --- --- --- --- --- --- --- --- --- --- --- --- --- --- --- ---
         711         720         729         738         747         756
   TCT CGA CCC TGT CCT CCC CCC GCC ACT GGA AGT CTT CCC GTC TCT AAA TGG AAT
   --- --- --- --- --- --- --- --- --- --- --- --- --- --- --- --- --- ---
         765         774         783         792         801         810
   TAG TGG AGC CCG GAG CCT CTG GTG TAA CGC ACA GAC ATG ATC CAT GGG CGC AGC
   --- --- --- --- --- --- --- --- --- --- --- --- --- --- --- --- --- ---
                                                     M   I   H   G   R   S
         819         828         837         846         855         864
   GTG CTT CAC ATT GTA GCA AGT TTA ATC ATC CTC CAT TTG TCT GGG GCA ACC AAG
   --- --- --- --- --- --- --- --- --- --- --- --- --- --- --- --- --- ---
    V   L   H   I   V   A   S   L   I   I   L   H   L   S   G   A   T   K
         873         882         891         900         909         918
   AAA GGA ACA GAA AAG CAA ACC ACC TCA GAA ACA CAG AAG TCA GTG CAG TGT GGA
   --- --- --- --- --- --- --- --- --- --- --- --- --- --- --- --- --- ---
    K   G   T   E   K   Q   T   T   S   E   T   Q   K   S   V   Q   C   G
```

FIG. 1B

```
          927         936         945         954         963         972
ACT TGG ACA AAA CAT GCA GAG GGA GGT ATC TTT ACC TCT CCC AAC TAT CCC AGC
--- --- --- --- --- --- --- --- --- --- --- --- --- --- --- --- --- ---
 T   W   T   K   H   A   E   G   G   I   F   T   S   P   N   Y   P   S 981         990         999        1008        1017        1026
AAG TAT CCC CCT GAC CGG GAA TGC ATC TAC ATC ATA GAA GCC GCT CCA AGA CAG
--- --- --- --- --- --- --- --- --- --- --- --- --- --- --- --- --- ---
 K   Y   P   P   D   R   E   C   I   Y   I   I   E   A   A   P   R   Q 1035        1044        1053        1062        1071        1080
TGC ATT GAA CTT TAC TTT GAT GAA AAG TAC TCT ATT GAA CCG TCT TGG GAG TGC
--- --- --- --- --- --- --- --- --- --- --- --- --- --- --- --- --- ---
 C   I   E   L   Y   F   D   E   K   Y   S   I   E   P   S   W   E   C 1089        1098        1107        1116        1125        1134
AAA TTT GAT CAT ATT GAA GTT CGA GAT GGA CCT TTT GGC TTT TCT CCA ATA ATT
--- --- --- --- --- --- --- --- --- --- --- --- --- --- --- --- --- ---
 K   F   D   H   I   E   V   R   D   G   P   F   G   F   S   P   I   I 1143        1152        1161        1170        1179        1188
GGA CGT TTC TGT GGA CAA CAA AAT CCA CCT GTC ATA AAA TCC AGT GGA AGA TTT
--- --- --- --- --- --- --- --- --- --- --- --- --- --- --- --- --- ---
 G   R   F   C   G   Q   Q   N   P   P   V   I   K   S   S   G   R   F 1197        1206        1215        1224        1233        1242
CTA TGG ATT AAA TTT TTT GCT GAT GGA GAG CTG GAA TCT ATG GGA TTT TCA GCT
--- --- --- --- --- --- --- --- --- --- --- --- --- --- --- --- --- ---
 L   W   I   K   F   F   A   D   G   E   L   E   S   M   G   F   S   A 1251        1260        1269        1278        1287        1296
CGA TAC AAT TTC ACA CCT GGT AAG TAA GTA CTT AAA AAA AAA ATT TCT TTT TCT
--- --- --- --- --- --- --- --- --- --- --- --- --- --- --- --- --- ---
 R   Y   N   F   T   P   G   K   *

1305        1314        1323        1332        1341        1350
TCC TCA TTT TTC TAT CTT CAT AGT ACA AAA TCT TGT GTA AGA CAA CAT TAT ACT
--- --- --- --- --- --- --- --- --- --- --- --- --- --- --- --- --- ---
         1359        1368        1377        1386        1395        1404
TTC TCA GAG AAT GTT CCA GTT CTA TTT AAA ACC AAA TCT ACA GTG CTT TTT CTT
--- --- --- --- --- --- --- --- --- --- --- --- --- --- --- --- --- ---
         1413        1422        1431        1440        1449        1458
TTC CCT ACA CAA ATT CTG AAA GGA AAA GAT GTT TTC CTT AAA ACA GCC TAT ACT
--- --- --- --- --- --- --- --- --- --- --- --- --- --- --- --- --- ---
         1467        1476        1485        1494        1503        1512
AGA GGT AAA GAG TAG TGA CTC AAG GCT CTA AAT GGG CAT CAG CCA CAT CAT CAA
--- --- --- --- --- --- --- --- --- --- --- --- --- --- --- --- --- ---
         1521        1530        1539        1548        1557        1566
GTG GAC TTT TGT TAT GAT GGA ATG TGT AAT TGG AGA GAC AGT CTG TGA TAA GGA
--- --- --- --- --- --- --- --- --- --- --- --- --- --- --- --- --- ---
         1575        1584        1593        1602        1611        1620
AAC TAT ACA TAG GAG CTG AAT AAA CTT GAA AAG ACA ATT GTA GTA TTA TAA AAT
--- --- --- --- --- --- --- --- --- --- --- --- --- --- --- --- --- ---
         1629        1638        1647        1656        1665        1674
ATA TCC ACC AAA ATG ATC TTT GGG GAA CTT GAA TCA AAA GTT TAT TTG TTC TGA
--- --- --- --- --- --- --- --- --- --- --- --- --- --- --- --- --- ---
         1683        1692        1701        1710        1719        1728
AAA TTA CCG TGT TTC AAT CAA ATA GAT CCT ACT TTA GGA AGT AGT CTG CTC TCT
--- --- --- --- --- --- --- --- --- --- --- --- --- --- --- --- --- ---
         1737        1746        1755        1764        1773        1782
TTT CAG GAA AGC AAA TTC TTA AGA GTT TTG ATG AAA GGA AAA CTG AGA CCT GTA
--- --- --- --- --- --- --- --- --- --- --- --- --- --- --- --- --- ---
```

FIG. 1C

```
          1791        1800        1809        1818        1827        1836
ACA GCC AAA TAC TCA TTT ACA AGG TCT TGC AGA AAT TGT GTG CAA TTA TCA AAT
--- --- --- --- --- --- --- --- --- --- --- --- --- --- --- --- --- ---
          1845        1854        1863        1872        1881        1890
TAT GCA ATC TGT ATC AAT TTT CCT TTT AAC TCG CTA GAA TTA AAA AGA TCC TGT
--- --- --- --- --- --- --- --- --- --- --- --- --- --- --- --- --- ---
          1899        1908        1917        1926        1935        1944
GTT GTT GCC TGG CCC ACT TGA TTA AGA GTT ACC ATT CAT TAC AAT AAA AAT AGG
--- --- --- --- --- --- --- --- --- --- --- --- --- --- --- --- --- ---
          1953        1962        1971        1980        1989        1998
TTA TCA CAT TTT TTC ACT GCA AGA ACA CTA CAT GCA TTA ATT TAA ATG GAA AAA
--- --- --- --- --- --- --- --- --- --- --- --- --- --- --- --- --- ---
          2007        2016        2025        2034        2043        2052
TGA TTC AAA TTA CAT AAA GCC CAT TTT TTA TAT AGT TTG TTT TCA GTT TGT ATG
--- --- --- --- --- --- --- --- --- --- --- --- --- --- --- --- --- ---
          2061        2070        2079        2088        2097        2106
TAT TGT TTT ATT TAA GTT AGG CAA TAG CAT AAT TTC AAA TAT ATG TAA AGT TGG
--- --- --- --- --- --- --- --- --- --- --- --- --- --- --- --- --- ---
          2115        2124        2133        2142        2151        2160
TTG AAG TTT GTA TTC CAT GTT AAA GAA GTA ACA TCT AAA TAC AGC TTT GAT ACT
--- --- --- --- --- --- --- --- --- --- --- --- --- --- --- --- --- ---
          2169        2178        2187        2196        2205        2214
CAG TTA AAA AAC TAA AAT TTT AAA AAT TAT TAA TAT AAG TTT AAT GAT GAC TTT
--- --- --- --- --- --- --- --- --- --- --- --- --- --- --- --- --- ---
          2223        2232        2241        2250        2259        2268
CAT TAT GAC ATC ATG GGG TAT GTT AAA TCA AGT ATT TAC TGT AGC ATA TAT ATT
--- --- --- --- --- --- --- --- --- --- --- --- --- --- --- --- --- ---
          2277        2286        2295        2304        2313        2322
AGC TTT AAG CAT TAG GAA TGT TTT TAA TAA TAT CAC TAA AGG ATT GTG GTT TTA
--- --- --- --- --- --- --- --- --- --- --- --- --- --- --- --- --- ---
          2331        2340        2349        2358        2367        2376
ATT ATG CTT TGC TGA TAA TGG ATT ACT CAC AGA AAT CAT GGG TAT TTC ATG TGC
--- --- --- --- --- --- --- --- --- --- --- --- --- --- --- --- --- ---
          2385        2394        2403        2412        2421        2430
TAC AGT CGA ACT AAT TTG AAG TAT TCC CAA AAG GTA CAA ATG TTA GCT TAA TTT
--- --- --- --- --- --- --- --- --- --- --- --- --- --- --- --- --- ---
          2439        2448        2457        2466        2475        2484
GTT TGT TCA GAT TAT TAG TGC TAG AGT TGT AAA TGG AAA GGT AGG TAT TTT TTT
--- --- --- --- --- --- --- --- --- --- --- --- --- --- --- --- --- ---
          2493        2502        2511        2520        2529        2538
CTT AAC TGA TAA TTT TGA ATA TAA CCT GTA CCT AGA GAC AGT GAC ATA CGG CAT
--- --- --- --- --- --- --- --- --- --- --- --- --- --- --- --- --- ---
          2547        2556        2565        2574        2583        2592
GTT CTA GGT TTC ATA AGT TAT ATT TTC ATT CTG GGT TTG GTG ATC ATG AAA ATA
--- --- --- --- --- --- --- --- --- --- --- --- --- --- --- --- --- ---
          2601        2610        2619        2628        2637
ATG TCT TGG ATT TAA AAT TGT GGT TTC ACA AAA AAA AAA AAA AAA AA 3'
--- --- --- --- --- --- --- --- --- --- --- --- --- --- --- --
```

FIG. 3

A 43.5% identity in 115 residues overlap

```
BPC-1        33 IFTSPNYPSKYPPDRECIYIIEAAPRQCIELYFDEKYSIEPSW-------ECKFDHIEVR
CUB domain   75 IFTSPNFPDRYPPNIDCVRVIHSRPQHDVVVKFHHVFHIESTYDKIDAGEECPNDFIEFR
                ****** * ***  *  *  *       **        **  * **  *

BPC-1        86 DGPFGFSPIIGRFCGQQNPP-VIKSSGRFLWIKFFADGELESMGFSARYNFTPGK
CUB domain  135 DGRYGFSPLIARFCGDRMPKREIRAVSGFLWIRFRSDSMLEYQGFSAEYAIVPSK
                ** **** * ****  *  *    **** *  * ** **** *   *  *
```

B 35.3% identity in 102 residues overlap in CUB domain 1 of BMP-1

```
BPC-1       130 GIFTSPNYPSKYPPDRECIYIIEAAPRQCIELYFDEKYSIEPSWECKFDHIEVRDGPFGF
BMP-1       336 GNFSSPEYPNGYSAHMHCVWRISVTPGEKIILNFTSM-DLYRSRLCWYDYVEVRDGFWRK
                *  ** **   *     *   *    *  * *       *    *  * ****  *
```

```
BPC-1       190 SPIIGRFCGQQNPPVIKSSGRFLWIKFFADGELESMGFSARY
BMP-1       395 VWVRGRFCGGKLPEPIVSTDSRLWVEFRSSSNWVGKFFAVY
                     ****   *  *  *   ** *       **  *
```

39.4% identity in 104 residues overlap in CUB domain 2 of BMP-1

```
BPC-1       128 EGGIFTSPNYPSKYPPDRECIYIIEAAPRQCIELYFDEKYSIEPSWECKFDHIEVRDGPF
BMP-1       447 DNGHIQSPNYPDDYRPSKVCIWRIQVSEGFHVGLTF-QSFEIERHDSCAYDYLEVRDGHS
                  *  ***** * *  **  *    *    *        **       *   *****
```

```
BPC-1       188 GFSPIIGRFCGQQNPPVIKSSGRFLWIKFFADGELESMGFSARY
BMP-1       506 ESSNLIGRYCGYENPDDIKSTSSRLWLKFVSDGSINKAGFAVNF
                *   *** **  **  ** *** **  *   *     **
```

36.3% identity in 102 residues overlap in CUB domain 3 of BMP-1

```
BPC-1       130 GIFTSPNYPSKYPPDRECIYIIEAAPRQCIELYFDEKYSIEPSWECKFDHIEVRDGPFGF
BMP-1       605 GSITSPGWPKEYPPNKNCIWQLVAPTQYRISLQFDF-FETEGNDVCKYDFVEVRSGLTAD
                 * *** **  * ***  **    *    * *  *      **  * *** ***  *
```

```
BPC-1       190 SPIIGRFCGQQNPPVIKSSGRFLWIKFFADGELESMGFSARY
BMP-1       664 SKLHGKFCGSEKPEVITSQYNNMRVEFKSDNTVSKKGFKAHF
                *   * ***  *  * **           *   **   **
```

37.9% identity in 103 residues overlap in CUB domain 4 of BMP-1

```
BPC-1       130 GIFTSPNYPSKYPPDRECIYIIEAAPRQCIELYFDEKYSIEPSWECKFDHIEVRDGPFGF
BMP-1       761 GTITSPNWPDKYPSKKECTWAISSTPGHRVKLTFVEM-DIESQPECAYDHLEVFDGRDAK
                * **** * *  ** ** **    *    *   *     **    ** **  ** **  **
```

```
BPC-1       190 SPIIGRFCGQQNPPVIKSSGRFLWIKFFADGELESMGFSARYN
BMP-1       820 APVLGRFCGSKKPEPVLATGNRMFLRFYSDNSVQRKGFQASHS
                  * ***** *  **            * *  *       **  *
```

32.3% identity in 96 residues overlap in CUB domain 5 of BMP-1

```
BPC-1       139 SKYPPDRECIYIIEAAPRQCIELYFDEKYSIEPSWECKFDHIEVRDGPFGFSPIIGRFCG
BMP-1       887 NNYPGGVDCEWVIVAEEGYGVELVF-QTFEVEEETDCGYDYIELFDGYDSTAPRLGRYCG
                 **  *  *   * *       **     *      *  *  * *    ** * ** **
```

```
BPC-1       199 QQNPPVIKSSGRFLWIKFFADGELESMGFSARYNFT
BMP-1       946 SGPPEEVYSAGDSVLVKFHSDDTISKKGFHLRYTST
                   *   *  **  **   **   **  *   *
```

FIG. 4
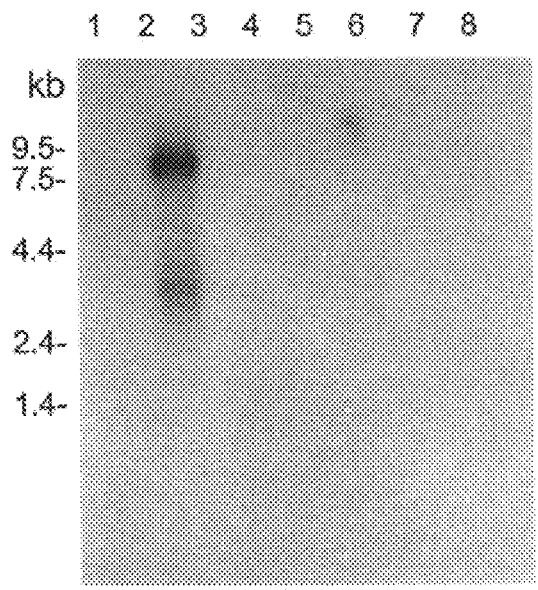
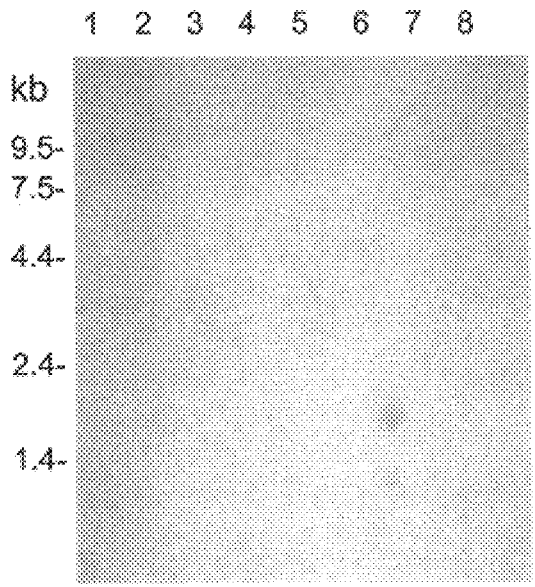
A
1. Heart
2. Brain
3. Placenta
4. Lung
5. Liver
6. Skeletal Muscle
7. Kidney
8. Pancreas
B
1. Spleen
2. Thymus
3. Prostate
4. Testis
5. Ovary
6. Small Intestine
7. Colon
8. Leukocytes

FIG. 5
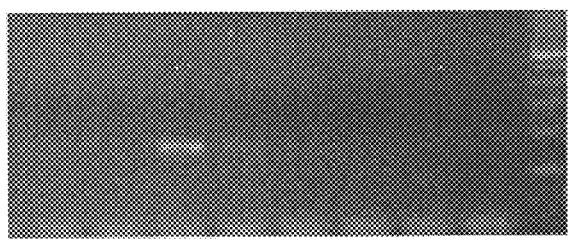
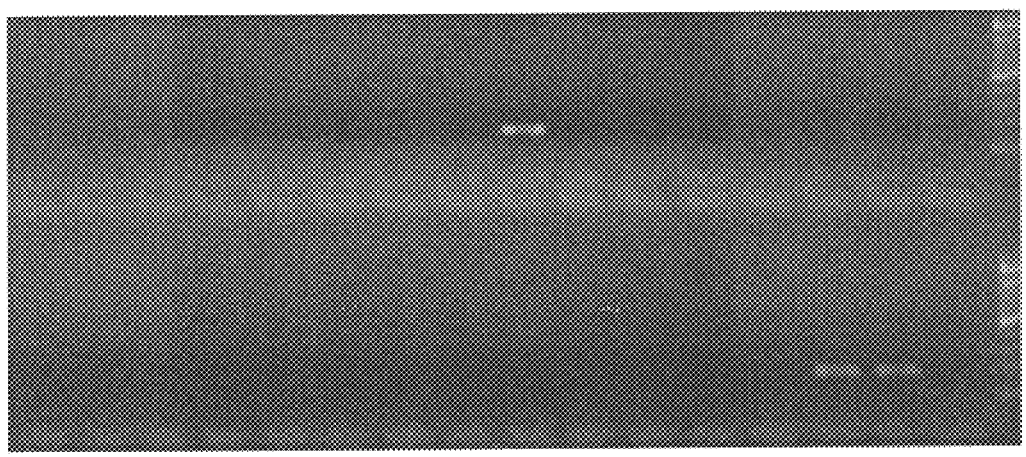
Panels:
A
1. Brain
2. Prostate
3. LAPC-4 AD
4. LAPC-4 AI
5. LAPC-9 AD
6. HeLa
7. Murine cDNA
8. Neg. control
B
1. Brain
2. Heart
3. Kidney
4. Liver
5. Lung
6. Pancreas
7. Placenta
8. Skeletal Muscle
C
1. Colon
2. Ovary
3. Leukocytes
4. Prostate
5. Small Intestine
6. Spleen
7. Testis
8. Thymus

FIG. 6

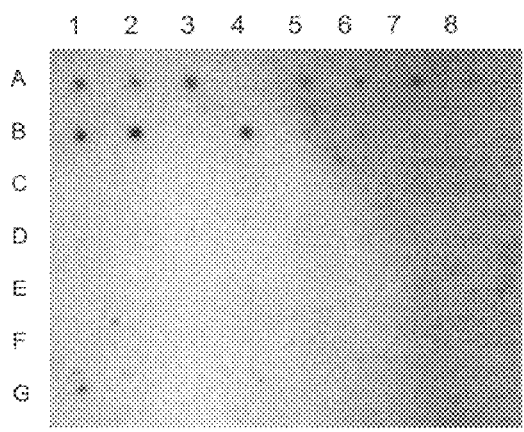

A1 brain
A2 amygdala
A3 caudate nucleus
A4 cerebellum
A5 cerebral cortex
A6 frontal lobe
A7 hippocampus
A8 medulla oblongata B1 occipital lobe
B2 putamen
B3 substantia nigra
B4 temporal lobe
B5 thalamus
B6 sub-thalamic nucleus
B7 spinal cord C1 heart
C2 aorta
C3 skeletal muscle
C4 colon
C5 bladder
C6 uterus
C7 prostate
C8 stomach D1 testis
D2 ovary
D3 pancreas
D4 pituitary gland
D5 adrenal gland
D6 thyroid gland
D7 salivary gland
D8 mammary gland E1 kidney
E2 liver
E3 small intestine
E4 spleen
E5 thymus
E6 peripheral leukocytes
E7 lymph node
E8 bone marrow F1 appendix
F2 lung
F3 trachea
F4 placenta G1 fetal brain
G2 fetal heart
G3 fetal kidney
G4 fetal liver
G5 fetal spleen
G6 fetal thymus
G7 fetal lung anti-BPC-1

Lanes:

1. HighFive cell extract - uninfected
2. HighFive cell extract - infected with BPC-1 virus
3. HighFive cell extract - infected with BPC-1 virus
4. HighFive cell media - infected with BPC-1 virus
5. HighFive cell media - infected with BPC-1 virus 1. PC3/neo
2. PC3/BPC-1
3. 3T3CL7/neo, acute infection
4. 3T3CL7/BPC-1, acute infection FIG. 15
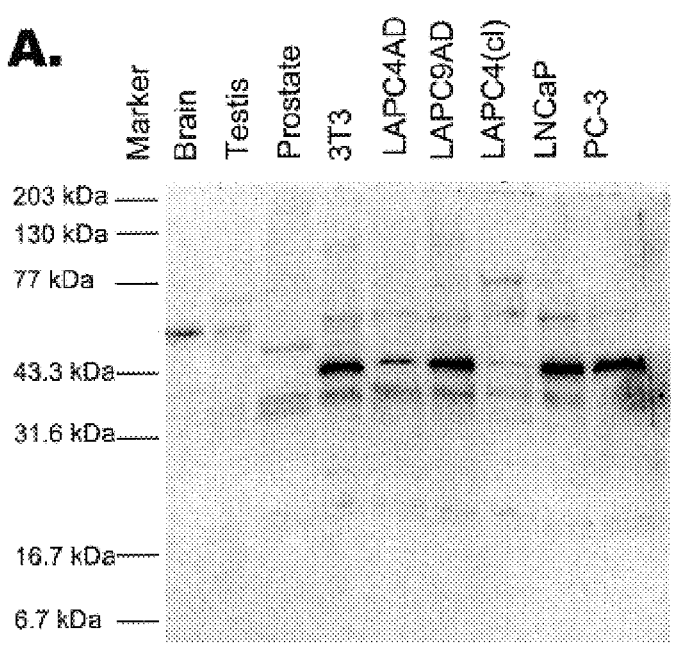
BPC-1-AP Conditioned Media
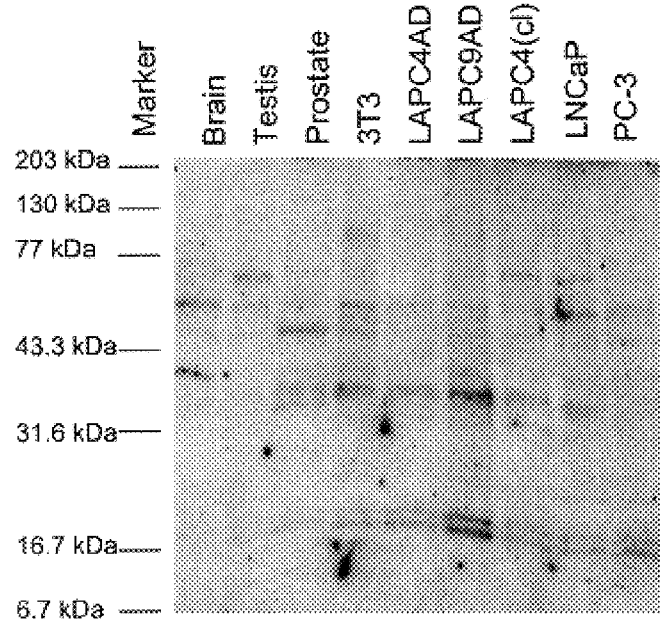
Alkaline Phosphatase Conditioned Media

BPC-1: A SECRETED BRAIN-SPECIFIC PROTEIN EXPRESSED AND SECRETED BY PROSTATE AND BLADDER CANCER CELLS

This application claims the benefit of U.S. provisional patent application number 60/095,982, filed Aug. 10, 1998, now abandoned, the entire contents of which are incorporated herein by reference.

FIELD OF THE INVENTION

The invention described herein relates to a novel gene and its encoded secreted tumor antigen, termed BPC-1, and to diagnostic and therapeutic methods and compositions useful in the management of various cancers which express BPC-1, particularly including prostate cancer and bladder cancer.

BACKGROUND OF THE INVENTION

Cancer is the second leading cause of human death next to coronary disease. Worldwide, millions of people die from cancer every year. In the United States alone, cancer causes the death of well over a half-million people each year, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Generally speaking, the fundamental problem in the management of the deadliest cancers is the lack of effective and non-toxic systemic therapies. Molecular medicine, still very much in its infancy, promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy remain fixed as the main treatment modalities. Unfortunately, these treatments are ineffective for many and are often associated with significant undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects, as further discussed below. Most prostate cancers initially occur in the peripheral zone of the prostate gland, away from the urethra. Tumors within this zone may not produce any symptoms and, as a result, most men with early-stage prostate cancer will not present clinical symptoms of the disease until significant progression has occurred. Tumor progression into the transition zone of the prostate may lead to urethral obstruction, thus producing the first symptoms of the disease. However, these clinical symptoms are indistinguishable from the common non-malignant condition of benign prostatic hyperplasia (BPH). Early detection and diagnosis of prostate cancer currently relies on digital rectal examinations (DRE), prostate specific antigen (PSA) measurements, transrectal ultrasonography (TRUS), and transrectal needle biopsy (TRNB). At present, serum PSA measurement in combination with DRE represent the leading tool used to detect and diagnose prostate cancer. Both have major limitations which have fueled intensive research into finding better diagnostic markers of this disease.

Similarly, there is no available marker that can predict the emergence of the typically fatal metastatic stage of prostate cancer. Diagnosis of metastatic stage is presently achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving diagnostic accuracy and opening therapeutic options. A similar problem is the lack of an effective prognostic marker for determining which cancers are indolent and which ones are or will be aggressive. PSA, for example, fails to discriminate accurately between indolent and aggressive cancers. Until there are prostate tumor markers capable of reliably identifying early-stage disease, predicting susceptibility to metastasis, and precisely imaging tumors, the management of prostate cancer will continue to be extremely difficult.

PSA is the most widely used tumor marker for screening, diagnosis, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not a disease-specific marker, as elevated levels of PSA are detectable in a large percentage of patients with BPH and prostatitis (25–86%)(Gao et al., 1997, Prostate 31: 264–281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and visa-versa. Moreover, it is now recognized that PSA is not prostate-specific (Gao et al., supra, for review).

Various methods designed to improve the specificity of PSA-based detection have been described, such as measuring PSA density and the ratio of free vs. complexed PSA. However, none of these methodologies have been able to reproducibly distinguish benign from malignant prostate disease. In addition, PSA diagnostics have sensitivities of between 57–79% (Cupp & Osterling, 1993, Mayo Clin Proc 68:297–306), and thus miss identifying prostate cancer in a significant population of men with the disease.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759–766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95:1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC-4 cDNA and is unique in that it is expressed primarily in basal cells of normal prostate tissue and in cancer epithelia (Reiter et al., 1998). Vaccines for prostate cancer are also being actively explored with a variety of antigens, including PSM and PSA.

SUMMARY OF THE INVENTION

The present invention relates to a novel secreted protein designated BPC-1. In normal individuals, BPC-1 protein is only expressed in certain tissues of the brain. In prostate cancer, BPC-1 is expressed at high levels in tumor cells. BPC-1 is also expressed in bladder cancer cells, and may be expressed in other cancer cells. The structure of BPC-1 includes a signal sequence and a CUB domain. The BPC-1 protein CUB domain is structurally similar to the CUB domains of several other proteins.

The BPC-1 gene therefore encodes a secreted tumor antigen which may be useful as a diagnostic, staging and/or prognostic marker, and/or may serve as an excellent target for various approaches to the treatment of prostate, bladder and other cancers expressing BPC-1. Although the precise function of BPC-1 is presently unknown, preliminary experimental evidence suggests that BPC-1 is directly involved in oncogenesis or maintenance of the transformed phenotype of cancer cells expressing BPC-1. BPC-1 also appears to bind specifically to a cellular protein expressed in prostate cancer cells and other cells. Taken together, this evidence indicates that BPC-1 is functionally involved in an oncogenic pathway. As further described herein, this understanding leads to a number of potential approaches to the treatment of cancers expressing BPC-1 involving the inhibition of BPC-1 function.

The invention provides polynucleotides corresponding or complementary to all or part of the BPC-1 genes, mRNAs, and/or coding sequences, preferably in isolated form, including polynucleotides encoding BPC-1 proteins and fragments thereof, DNA, RNA, DNA/RNA hybrid, and related molecules, polynucleotides or oligonucleotides complementary to the BPC-1 genes or mRNA sequences or parts thereof, and polynucleotides or oligonucleotides which hybridize to the BPC-1 genes, mRNAs, or to BPC-1-encoding polynucleotides. Also provided are means for isolating cDNAs and the genes encoding BPC-1. Recombinant DNA molecules containing BPC-1 polynucleotides, cells transformed or transduced with such molecules, and host-vector systems for the expression of BPC-1 gene products are also provided. The invention further provides BPC-1 proteins and polypeptide fragments thereof. The invention further provides antibodies that bind to BPC-1 proteins and polypeptide fragments thereof, including polyclonal and monoclonal antibodies, murine and other mammalian antibodies, chimeric antibodies, humanized and fully human antibodies, antibodies labeled with a detectable marker, and antibodies conjugated to radionuclides, toxins or other therapeutic compositions. The invention further provides methods for detecting the presence of BPC-1 polynucleotides and proteins in various biological samples, as well as methods for identifying cells that express a BPC-1. The invention further provides various therapeutic compositions and strategies for treating cancers which express BPC-1 such as prostate and bladder cancers, including antibody, vaccine and small molecule therapy, and therapies aimed at inhibiting the transcription, translation, processing or function of BPC-1.

BRIEF DESCRIPTION OF THE FIGURES

FIGS. 1(A, B, and C). Molecular structure of human BPC-1: Nucleotide and deduced amino acid sequences of BPC-1 clone 6 cDNA (SEQ ID NOS: 1 and 2, respectively). The signal sequence is indicated in boldface, the CUB domain in underlined boldface, and the SSH-derived nucleic acid sequence in boldface.

FIG. 3. Molecular structure of human BPC-1: Amino acid sequence alignment of the BPC-1 CUB domain with CUB domains from various known proteins. (A) Alignment of BPC-1 with C. elegans CUB domain protein (Wilson et al., 1994, Nature 368:32–38) (SEQ ID NO. 3), and (B) alignments with the CUB domains of murine BMP-1 (Fukagawa et al. 1994, Dev. Biol 163: 175–183) (SEQ ID NOS: 4–8). Percent sequence identities are indicated on the figure.

FIG. 4. Northern blot analysis of human BPC-1 expression in various normal tissues showing exclusive expression in brain.

FIG. 5. Semi-quantitative RT-PCR expression analysis showing human BPC-1 expression in prostate cancer xenografts (lanes 3–5 of panel A) and a limited number of normal human tissues (lanes 1–2 of panel A; lanes 1–8 of panels B and C).

FIG. 6. RNA dot blot analysis of human BPC-1 mRNA expression in 37 normal tissues, showing expression only in specific regions of the brain.

FIG. 15. BPC-1-AP binds to a 45 kDa protein using a far-western analysis. Lysates from brain, testis, prostate, the xenografts LAPC4AD and LAPC9AD, and the cell lines 3T3, LAPC4, LNCaP, and PC-3 were used to make the western blots. The blots were incubated with conditioned media from a 293T cell line producing only secreted alkaline phosphatase (B) and with media containing BPC-1-AP (A). The alkaline phosphatase signals were detected using a chemiluminescent AP detection system.

DETAILED DESCRIPTION OF THE INVENTION

Figure 2:
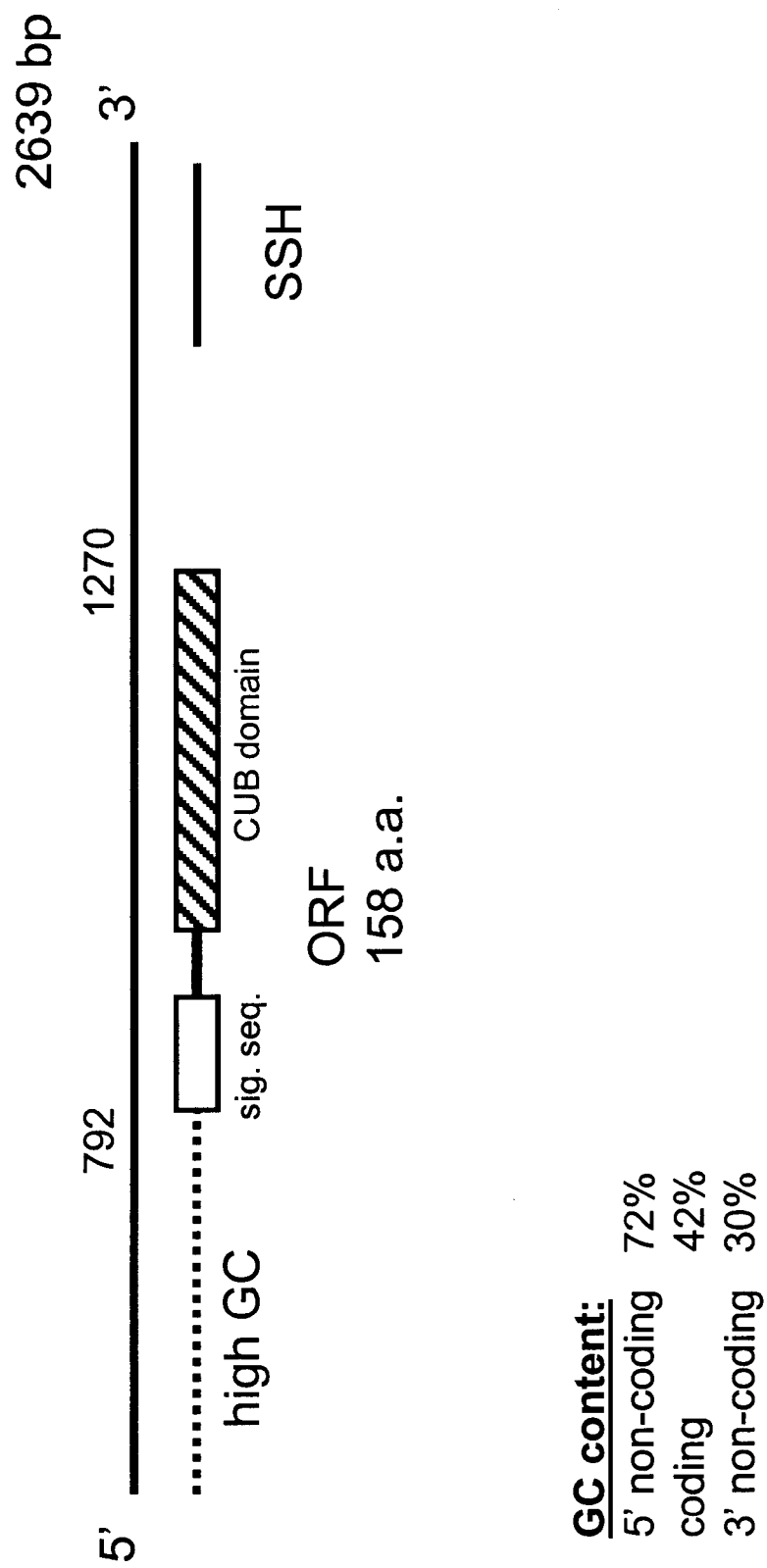
FIG. 2. Molecular structure of human BPC-1: Schematic representation of the human BPC-1 structure. Percentage CG contents across regions of the sequence are also indicated.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers which have extended through the prostate capsule, and are meant to include stage C disease under the American Urological Association (AUA) system, stage C1–C2 disease under the Whitmore-Jewett system, and stage T3–T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees C and temperatures for washing in 0.1×SSC/0.1% SDS are above 55 degrees C, and most preferably to stringent hybridization conditions.

In the context of amino acid sequence comparisons, the term "identity" is used to express the percentage of amino acid residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

MOLECULAR AND BIOCHEMICAL FEATURES OF BPC-1

As is further described in the Examples which follow, the BPC-1 gene and protein have been characterized using a number of analytical approaches. For example, analyses of nucleotide coding and amino acid sequences were conducted in order to identify potentially related molecules, as well as recognizable structural domains, topological features, and other elements within the BPC-1 mRNA and protein structure. RT-PCR and Northern blot analyses of BPC-1 mRNA expression were conducted in order to establish the range of normal and cancerous tissues expressing BPC-1 message. Western blot analyses of BPC-1 protein expression in experimentally transfected cells were conducted to determine cell localization and secretion of processed and unprocessed recombinant human BPC-1 protein. Functional assays designed to determine BPC-1 interaction with cellular binding partner(s) and activity were also conducted.

BPC-1 is an oncogenic, secreted, CUB domain-containing protein which is expressed in prostate and bladder carcinoma cells and binds to a cellular protein. BPC-1 expression is exquisitely brain-specific in normal adult human tissues. In fetal tissues, BPC-1 expression is predominant in brain, but is also turned on in a number of other developing organs and tissues. BPC-1 gene expression is activated in human prostate cancer. In particular, BPC-1 is expressed at very high levels in androgen dependent human prostate tumor xenografts originally derived from a patient with high grade metastatic prostate cancer, and is expressed at lower but significant levels in other prostate cancer samples. BPC-1 is also expressed at high levels in at least some bladder carcinomas.

The BPC-1 protein is initially translated into a 158 amino acid precursor containing a signal sequence. During post-translational processing, the signal sequence is cleaved to yield the mature 135 amino acid secreted protein. The 5' non-coding region of the BPC-1 gene is extremely G/C rich (approximately 72% G/C content, compared to 42% in the coding region and 30% in the 3' non-coding region), implying that this region of the gene contains elements involved in transcriptional or translational control (FIG. 1) (SEQ ID NO. 1).

The BPC-1 primary structure (SEQ ID NO. 2) contains a recognizable CUB domain (Complement subcomponents C1r/C1s, Uegf, Bmp1)(Borck and Beckmann, 1993, J. Mol. Biol. 231: 539–545) which shares homology with other CUB domain proteins (FIG. 1; FIG. 3). CUB domains were originally found in complement subcomponents C1r and C1s, and were subsequently identified in Uegf (epidermal growth factor related sea urchin protein) and Bmp1 (bone morphogenetic protein 1), a protease involved in bone development. Functionally, CUB domains have been associated with protein interaction, receptor binding and other activities. Unlike other CUB domain proteins which have additional enzymatic functions, BPC-1 is unique in that it is essentially a secreted CUB domain with no other apparent functional domains. The CUB domain of BPC-1 could function as a protein-protein interaction domain, mediating interactions with other secreted molecules, extracellular matrix molecules and/or cell surface receptors. This would imply a potential growth-factor or cell stimulator function.

The presence of a CUB domain in the BPC-1 structure further supports the conclusion that BPC-1 interacts with and probably binds to other proteins. The CUB domain, viewed as an extracellular domain involved in protein-protein interaction, occurs in many diverse secreted or cell surface proteins involved in a variety developmental processes (Borck and Beckmann, 1993, J. Mol. Biol. 231: 539–545). One family of proteins characterized by CUB domains, to which BPC-1 protein may bear some relation, are the Spermadhesins. The Spermadhesins are CUB domain containing secreted proteins produced by the seminal vesicles and are estimated to be about 15–18 kd in size (approx. 140 amino acids); these proteins function to inhibit sperm motility and are inactivated by proteolysis (Iwamoto et al., 1995, FEBBS Letters 368: 420–424).

Preliminary experimental evidence suggests that BPC-1 is directly involved in oncogenesis or maintenance of the transformed phenotype of cancer cells expressing BPC-1. In this regard, BPC-1 shows transforming activity in soft agar assays and binds to a cellular protein expressed by cells including those expressing BPC-1. Taken together, this evidence indicates that BPC-1 is functionally involved in an oncogenic pathway, and that BPC-1 activity in this pathway may occur through interaction with a BPC-1 binding partner or through binding to or association with other protein(s). As further described herein, this understanding leads to a number of potential approaches to the treatment of cancers expressing BPC-1, involving the inhibition of BPC-1 function.

BPC-1 POLYNUCLEOTIDES

One aspect of the invention provides polynucleotides corresponding or complementary to all or part of a BPC-1 gene, mRNA, and/or coding sequence, preferably in isolated form, including polynucleotides encoding a BPC-1 protein and fragments thereof, DNA, RNA, DNA/RNA hybrid, and related molecules, polynucleotides or oligonucleotides complementary to a BPC-1 gene or mRNA sequence or a part thereof, and polynucleotides or oligonucleotides which hybridize to a BPC-1 gene, mRNA, or to a BPC- 1-encoding polynucleotide (collectively, "BPC-1 polynucleotides"). As used herein, the BPC-1 gene and protein is meant to include the BPC-1 gene and protein specifically described herein and the genes and proteins corresponding to other BPC-1 proteins and structurally similar variants of the foregoing. Such other BPC-1 proteins and variants will generally have coding sequences which are highly homologous to the BPC-1 and/or BPC-1-2 coding sequences, and preferably will share at least about 50% amino acid identity and at least about 60% amino acid homology (using BLAST criteria), more preferably sharing 70% or greater homology (using BLAST criteria).

A BPC-1 polynucleotide may comprise a polynucleotide having the nucleotide sequence of human BPC-1 as shown in FIG. 1 (SEQ ID NO. 1), a sequence complementary to the foregoing, or a polynucleotide fragment of any of the foregoing. Another embodiment comprises a polynucleotide which is capable of hybridizing under stringent hybridization conditions to the human BPC-1 cDNA shown in FIG. 1 (SEQ ID NO. 1) or to a polynucleotide fragment thereof.

Specifically contemplated are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the BPC-1 polynucleotides and polynucleotide sequences disclosed herein.

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a BPC-1 polynucleotide in a sample and as a means for detecting a cell expressing a BPC-1 protein. Examples of such probes include polypeptides comprising all or part of the human BPC-1 cDNA sequence shown in FIG. 1 (SEQ ID NO. 1). Examples of primer pairs capable of specifically amplifying BPC-1 mRNAs are also described in the Examples which follow. As will be understood by the skilled artisan, a great many different primers and probes may be prepared based on the sequences provided in herein and used effectively to amplify and/or detect a BPC-1 mRNA. As used herein, a polynucleotide is said to be "isolated" when it is substantially separated from contaminant polynucleotides which correspond or are complementary to genes other than the BPC-1 gene or which encode polypeptides other than BPC-1 gene product or fragments thereof. A skilled artisan can readily employ nucleic acid isolation procedures to obtain an isolated BPC-1 polynucleotide.

The BPC-1 polynucleotides of the invention are useful for a variety of purposes, including but not limited to their use as probes and primers for the amplification and/or detection of the BPC-1 gene(s), mRNA(s), or fragments thereof; as reagents for the diagnosis and/or prognosis of prostate cancer and other cancers; as coding sequences capable of directing the expression of BPC-1 polypeptides; as tools for modulating or inhibiting the expression of the BPC-1 gene (s) and/or translation of the BPC-1 transcript(s); and as therapeutic agents.

METHODS FOR ISOLATING BPC-1-ENCODING NUCLEIC ACID MOLECULES

The BPC-1 cDNA sequences described herein enable the isolation of other polynucleotides encoding BPC-1 gene product(s), as well as the isolation of polynucleotides encoding BPC-1 gene product homologues, alternatively spliced isoforms, allelic variants, and mutant forms of the BPC-1 gene product. Various molecular cloning methods that can be employed to isolate full length cDNAs encoding a BPC-1 gene are well known (See, for example, Sambrook, J. et al., Molecular Cloning: A Laboratory Manual, 2d edition., Cold Spring Harbor Press, New York, 1989; Current Protocols in Molecular Biology. Ausubel et al., Eds., Wiley and Sons, 1995). For example, lambda phage cloning methodologies may be conveniently employed, using commercially available cloning systems (e.g., Lambda ZAP Express, Stratagene). Phage clones containing BPC-1 gene cDNAs may be identified by probing with a labeled BPC-1 cDNA or a fragment thereof. For example, in one embodiment, the BPC-1 cDNA (FIG. 1) (SEQ ID NO. 7) or a portion thereof can be synthesized and used as a probe to retrieve overlapping and full length cDNAs corresponding to a BPC-1 gene. The BPC-1 gene itself may be isolated by screening genomic DNA libraries, bacterial artificial chromosome libraries (BACs), yeast artificial chromosome libraries (YACs), and the like, with BPC-1 DNA probes or primers.

RECOMBINANT DNA MOLECULES AND HOST-VECTOR SYSTEMS

The invention also provides recombinant DNA or RNA molecules containing a BPC-1 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a BPC-1 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HghFive cell). Examples of suitable mammalian cells include various prostate cancer cell lines such LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a BPC-1 may be used to generate BPC-1 proteins or fragments thereof using any number of host-vector systems routinely used and widely known in the art.

A wide range of host-vector systems suitable for the expression of BPC-1 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, BPC-1 may be preferably expressed in several prostate cancer and non-prostate cell lines, including for example 293, 293T, rat-1, 3T3, PC-3, LNCaP and TsuPr1. The host-vector systems of the invention are useful for the production of a BPC-1 protein or fragment thereof. Such host-vector systems may be employed to study the functional properties of BPC-1 and BPC-1 mutations.

Mature recombinant human BPC-1 protein may be produced and secreted by mammalian cells transfected with a construct encoding precursor BPC-1. In a particular embodiment described in the Examples, 293T cells are transfected with an expression plasmid encoding the precursor form of BPC-1 (i.e., including the signal sequence) and mature BPC-1 protein is secreted into the cell culture medium where it may be conveniently isolated using standard purification methods. Mature recombinant human BPC-1 may also be produced by cells which process but do not secrete the mature protein. One example of such a system is a BPC-1 encoding baculovirus-infected cell. As described in the examples, such cells express and process high levels of BPC-1 intracellularly. The mature BPC-1 protein may be recovered, in such cases, from cell lysates using standard procedures. Whether the mature BPC-1 is secreted or is retained intracellularly by the host cell, BPC-1 may be affinity purified from media or cell lysates using BPC-1 antibodies.

Proteins encoded by the BPC-1 genes, or by fragments thereof, will have a variety of uses, including but not limited to generating antibodies and in methods for identifying ligands and other agents and cellular constituents that bind to a BPC-1 gene product Antibodies raised against a BPC-1 protein or fragment thereof may be useful in diagnostic and prognostic assays, imaging methodologies (including, particularly, cancer imaging), and therapeutic methods in the management of human cancers characterized by expression of a BPC-1 protein, including but not limited to cancer of the prostate. Various immunological assays useful for the detection of BPC-1 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods). BPC-1 proteins may also be particularly useful in generating cancer vaccines, as further described below.

BPC-1 Proteins

Another aspect of the present invention provides BPC-1 proteins and polypeptide fragments thereof. The BPC-1 proteins of the invention include those specifically identified herein, as well as allelic variants, conservative substitution variants and homologs that can be isolated/generated and characterized without undue experimentation following the methods outlined below. Fusion proteins which combine parts of different BPC-1 proteins or fragments thereof, as well as fusion proteins of a BPC-1 protein and a heterologous polypeptide are also included. Such BPC-1 proteins will be collectively referred to as the BPC-1 proteins, the proteins of the invention, or BPC-1. As used herein, the term "BPC-1 polypeptide" refers to a polypeptide fragment or a BPC-1 protein of at least 10 amino acids, preferably at least 15 amino acids.

A specific embodiment of a BPC-1 protein comprises a polypeptide having the amino acid sequence of human BPC-1 as shown in FIG. 1 (SEQ ID NO: 2), from about amino acid residue number 1 through about amino acid residue number 158 as shown therein. Another specific embodiment of a BPC-1 protein comprises a polypeptide having the amino acid sequence of human BPC-1 as shown in FIG. 1 (SEQ ID NO: 2), from about amino acid residue number 24 through about amino acid residue number 158 as shown therein.

In general, naturally occurring allelic variants of human BPC-1 will share a high degree of structural identity and homology (e.g., 90% or more identity). Typically, allelic variants of the BPC-1 proteins will contain conservative amino acid substitutions within the BPC-1 sequences described herein or will contain a substitution of an amino acid from a corresponding position in a BPC-1 homologue. One class of BPC-1 allelic variants will be proteins that share a high degree of homology with at least a small region of a particular BPC-1 amino acid sequence, but will further contain a radical departure form the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

BPC-1 proteins may be embodied in many forms, preferably in isolated form. As used herein, a protein is said to be "isolated" when physical, mechanical or chemical methods are employed to remove the BPC-1 protein from cellular constituents that are normally associated with the protein. A skilled artisan can readily employ standard purification methods to obtain an isolated BPC-1 protein. A purified BPC-1 protein molecule will be substantially free of other proteins or molecules which impair the binding of BPC-1 to antibody or other ligand. The nature and degree of isolation and purification will depend on the intended use. Embodiments of a BPC-1 protein include a purified BPC-1 protein and a functional, soluble BPC-1 protein. In one form, such functional, soluble BPC-1 proteins or fragments thereof retain the ability to bind antibody or other ligand.

The invention also provides BPC-1 polypeptides comprising biologically active fragments of the BPC-1 amino acid sequence, such as a polypeptide corresponding to part of the amino acid sequences for BPC-1 as shown in FIG. 1 (SEQ ID NO. 2). Such polypeptides of the invention exhibit properties of the BPC-1 protein, such as the ability to elicit the generation of antibodies which specifically bind an epitope associated with the BPC-1 protein.

BPC-1 polypeptides can be generated using standard peptide synthesis technology or using chemical cleavage methods well known in the art based on the amino acid sequences of the human BPC-1 proteins disclosed herein. Alternatively, recombinant methods can be used to generate nucleic acid molecules that encode a polypeptide fragment of a BPC-1 protein. In this regard, the BPC-1-encoding nucleic acid molecules described herein provide means for generating defined fragments of BPC-1 proteins. BPC-1 polypeptides are particularly useful in generating and characterizing domain specific antibodies (e.g., antibodies recognizing an extracellular or intracellular epitope of a BPC-1 protein), in identifying agents or cellular factors that bind to BPC-1 or a particular structural domain thereof, and in various therapeutic contexts, including but not limited to cancer vaccines. BPC-1 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-BPC-1 antibodies or in identifying cellular factors that bind to BPC-1.

In a specific embodiment described in the examples which follow, mature secreted BPC-1 is conveniently expressed in 293T cells transfected with a CMV-driven expression vector encoding BPC-1 with a C-terminal 6xHis and MYC tag (pcDNA3.1/mycHIS, Invitrogen). The secreted HIS-tagged BPC-1 in the culture media may be purified using a nickel column using standard techniques.

BPC-1 Antibodies

Another aspect of the invention provides antibodies that bind to BPC-1 proteins and polypeptides. The most preferred antibodies will selectively bind to a BPC-1 protein and will not bind (or will bind weakly) to non-BPC-1 proteins and polypeptides. Anti-BPC-1 antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule which binds to its target, i.e., the antigen binding region.

BPC-1 antibodies of the invention may be particularly useful in prostate cancer therapeutic strategies, diagnostic and prognostic assays, and imaging methodologies. Similarly, such antibodies may be useful in the treatment, diagnosis, and/or prognosis of other cancers, to the extent BPC-1 is also expressed or overexpressed in other types of cancer. One such cancer that expresses BPC-1 is bladder carcinoma.

The invention also provides various immunological assays useful for the detection and quantification of BPC-1 and mutant BPC-1 proteins and polypeptides. Such assays generally comprise one or more BPC-1 antibodies capable of recognizing and binding a BPC-1 or mutant BPC-1 protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer are also provided by the invention, including but limited to radioscintigraphic imaging methods using labeled BPC-1 antibodies. Such assays may be clinically useful in the detection, monitoring, and prognosis of prostate cancer, particularly advanced prostate cancer.

BPC-1 antibodies may also be used in methods for purifying BPC-1 and mutant BPC-1 proteins and polypeptides and for isolating BPC-1 homologues and related molecules. For example, in one embodiment, the method of purifying a BPC-1 protein comprises incubating a BPC-1 antibody, which has been coupled to a solid matrix, with a lysate or other solution containing BPC-1 under conditions which permit the BPC-1 antibody to bind to BPC-1; washing the solid matrix to eliminate impurities; and eluting the BPC-1 from the coupled antibody. Other uses of the BPC-1 antibodies of the invention include generating anti-idiotypic antibodies that mimic the BPC-1 protein.

BPC-1 antibodies may also be used therapeutically by, for example, modulating or inhibiting the biological activity of a BPC-1 protein or targeting and destroying cancer cells expressing a BPC-1 protein or BPC-1 binding partner. Because BPC-1 is a secreted protein which appears to bind to a cellular protein and because BPC-1 appears to have oncogenic activity, antibodies may be therapeutically useful for blocking BPC-1's ability to bind to its receptor or interact with other proteins through which it exerts its oncogenic biological activity. In a particular embodiment, a BPC-1 specific antibody or combination thereof (preferably a monoclonal antibody or combination thereof) is administered to a patient suffering from a BPC-1 expressing tumor such that the antibody binds to BPC-1 and inhibits its ability to execute its function. BPC-1 antibody therapy is more specifically described in the THERAPEUTIC METHODS AND COMPOSITIONS subsection below.

Various methods for the preparation of antibodies are well known in the art. For example, antibodies may be prepared by immunizing a suitable mammalian host using a BPC-1 protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of BPC-1 may also be used, such as a BPC-1 GST-fusion protein. In a particular embodiment, a GST fusion protein comprising all or most of the open reading frame amino acid sequence of FIG. 1 may be produced and used as an immunogen to generate appropriate antibodies. Cells expressing or overexpressing BPC-1 may also be used for immunizations. Similarly, any cell engineered to express BPC-1 may be used. Such strategies may result in the production of monoclonal antibodies with enhanced capacities for recognizing endogenous BPC-1. Another useful immunogen comprises BPC-1 proteins linked to the plasma membrane of sheep red blood cells. In addition, naked DNA immunization techniques known in the art may be used (with or without purified BPC-1 protein or BPC-1 expressing cells) to generate an immune response to the encoded immunogen (for review, see Donnelly et al., 1997, Ann. Rev. Immunol. 15:617–648).

The amino acid sequence of BPC-1 as shown in FIG. 1 (SEQ ID NO. 2) may be used to select specific regions of the BPC-1 protein for generating antibodies. For example, hydrophobicity and hydrophilicity analyses of the BPC-1 amino acid sequence may be used to identify hydrophilic regions in the BPC-1 structure. Regions of the BPC-1 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis.

Methods for the generation of BPC-1 antibodies are further illustrated by way of the examples provided herein.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a BPC-1 immunogen is conducted generally by injection over a suitable time period and with use of a suitable adjuvant, as is generally understood in the art. During the immunization schedule, titers of antibodies can be taken to determine adequacy of antibody formation.

BPC-1 monoclonal antibodies are preferred and may be produced by various means well known in the art. For example, immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the BPC-1 protein or BPC-1 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the BPC-1 protein can also be produced in the context of chimeric or CDR grafted antibodies of multiple species origin. Humanized or human BPC-1 antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522–525; Riechmnan et al., 1988, Nature 332: 323–327; Verhoeyen et al., 1988, Science 239: 1534–1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535–539).

Fully human BPC-1 monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human BPC-1 monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of BPC-1 antibodies with a BPC-1 protein may be established by a number of well known means, including Western blot, immunoprecipitation, ELISA, and FACS analyses using, as appropriate, BPC-1 proteins, peptides, BPC-1-expressing cells or extracts thereof.

A BPC-1 antibody or fragment thereof of the invention may be labeled with a detectable marker or conjugated to a second molecule, such as a cytotoxic agent, and used for targeting the second molecule to a BPC-1 positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). Examples of cytotoxic agents include, but are not limited to, ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, arbrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $^{212}$Bi, $^{131}$I, $^{131}$In, $^{90}$Y, and $^{186}$Re. Suitable detectable markers include, but are not limited to, a radioisotope, a fluorescent compound, a bioluminescent compound, chemiluminescent compound, a metal chelator or an enzyme. Antibodies may also be conjugated to an anti-cancer pro-drug activating enzyme capable of converting the pro-drug to its active form. See, for example, U.S. Pat. No. 4,975,287.

Further, bi-specific antibodies specific for two or more BPC-1 epitopes may be generated using methods generally known in the art. Further, antibody effector functions may be modified so as to enhance the therapeutic effect of BPC-1 antibodies on the growth of cancer cells. Homodimeric antibodies may also be generated by cross-linking techniques known in the art (e.g., Wolff et al., Cancer Res. 53: 2560–2565). Such antibodies may provide a means for achieving enhanced BPC-1 inhibition.

METHODS FOR THE DETECTION OF BPC-1

Another aspect of the present invention relates to methods for detecting BPC-1 polynucleotides and BPC-1 proteins, as well as methods for identifying a cell which expresses BPC-1.

More particularly, the invention provides assays for the detection of BPC-1 polynucleotides in a biological sample, such as serum, bone, prostate, and other tissues, urine, semen, cell preparations, and the like. Detectable BPC-1 polynucleotides include, for example, a BPC-1 gene or fragments thereof, BPC-1 mRNA, alternative splice variant BPC-1 mRNAs, and recombinant DNA or RNA molecules containing a BPC-1 polynucleotide. A number of methods for amplifying and/or detecting the presence of BPC-1 polynucleotides are well known in the art and may be employed in the practice of this aspect of the invention.

In one embodiment, a method for detecting a BPC-1 mRNA in a biological sample comprises producing cDNA from the sample by reverse transcription using at least one primer; amplifying the cDNA so produced using a BPC-1 polynucleotides as sense and antisense primers to amplify BPC-1 cDNAs therein; and detecting the presence of the amplified BPC-1 cDNA. In another embodiment, a method of detecting a BPC-1 gene in a biological sample comprises first isolating genomic DNA from the sample; amplifying the isolated genomic DNA using BPC-1 polynucleotides as sense and antisense primers to amplify the BPC-1 gene therein; and detecting the presence of the amplified BPC-1 gene. Any number of appropriate sense and antisense probe combinations may be designed from the nucleotide sequences provided for BPC-1 (FIG. 1) (SEQ ID NO. 2) and used for this purpose. The invention also provides assays for detecting the presence of a BPC-1 protein in a tissue of other biological sample such as serum, bone, prostate, and other tissues, urine, cell preparations, and the like. Methods for detecting a BPC-1 protein are also well known and include, for example, immunoprecipitation, immunohistochemical analysis, Western Blot analysis, molecular binding assays, ELISA, ELIFA and the like. For example, in one embodiment, a method of detecting the presence of a BPC-1 protein in a biological sample comprises first contacting the sample with a BPC-1 antibody, a BPC-1-reactive fragment thereof, or a recombinant protein containing an antigen binding region of a BPC-1 antibody; and then detecting the binding of BPC-1 protein in the sample thereto.

Methods for identifying a cell which expresses BPC-1 are also provided. In one embodiment, an assay for identifying a cell which expresses a BPC-1 gene comprises detecting the presence of BPC-1 mRNA in the cell. Methods for the detection of particular mRNAs in cells are well known and include, for example, hybridization assays using complementary DNA probes (such as in situ hybridization using labeled BPC-1 riboprobes, Northern blot and related techniques) and various nucleic acid amplification assays (such as RT-PCR using complementary primers specific for BPC-1, and other amplification type detection methods, such as, for example, branched DNA, SISBA, TMA and the like). Alternatively, an assay for identifying a cell which expresses a BPC-1 gene comprises detecting the presence of BPC-1 protein in the cell or secreted by the cell. Various methods for the detection of proteins are well known in the art and may be employed for the detection of BPC-1 proteins and BPC-1 expressing cells.

BPC-1 expression analysis may also be useful as a tool for identifying and evaluating agents which modulate BPC-1 gene expression. For example, BPC-1 expression is significantly upregulated in prostate cancer, and may also be expressed in other cancers. Identification of a molecule or biological agent that could inhibit BPC-1 expression or over-expression in cancer cells may be of therapeutic value. Such an agent may be identified by using a screen that quantifies BPC-1 expression by RT-PCR, nucleic acid hybridization or antibody binding.

ASSAYS FOR DETERMINING BPC-1 EXPRESSION STATUS

Determining the status of BPC-1 expression patterns in an individual may be used to diagnose cancer and may provide prognostic information useful in defining appropriate therapeutic options. Similarly, the expression status of BPC-1 may provide information useful for predicting susceptibility to particular disease stages, progression, and/or tumor aggressiveness. The invention provides methods and assays for determining BPC-1 expression status and diagnosing cancers which express BPC-1, such as prostate and bladder cancers.

In one aspect, the invention provides assays useful in determining the presence of cancer in an individual, such as prostate and bladder cancers, comprising detecting a significant increase in BPC-1 mRNA or protein expression in a test cell or tissue sample relative to expression levels in the corresponding normal cell or tissue. The presence of BPC-1 mRNA may, for example, be evaluated in tissue samples of the colon, lung, prostate, pancreas, bladder, breast, ovary, cervix, testis, head and neck, brain, stomach, etc. The presence of significant BPC-1 expression in any of these tissues may be useful to indicate the emergence, presence and/or severity of these cancers, since the corresponding normal tissues do not express BPC-1 mRNA or express it at lower levels.

In a related embodiment, BPC-1 expression status may be determined at the protein level rather than at the nucleic acid level. For example, such a method or assay would comprise determining the level of BPC-1 protein expressed by cells in a test tissue sample or in serum, semen or urine, and comparing the level so determined to the level of BPC-1 expressed in a corresponding normal sample. In one embodiment, the presence of BPC-1 protein is evaluated, for example, using immunohistochemical methods. BPC-1 antibodies or binding partners capable of detecting BPC-1 protein expression may be used in a variety of assay formats well known in the art for this purpose. In another embodiment, the presence of secreted BPC-1 protein in serum or urine or other body fluids is examined.

Because BPC-1 is a secreted protein expressed in prostate, bladder, and possibly other cancers, assays for detecting and quantifying BPC-1 in blood or serum are expected to be useful for the detection, diagnosis, prognosis, and/or staging of a BPC-1 expressing tumor in an individual. For example, BPC-1 is not expressed in normal prostate, but is expressed in prostate and bladder cancers. Accordingly, detection of serum BPC-1 may provide an indication of the presence of a prostate or bladder tumor. Diagnosis of prostate or bladder cancer may be made on the basis of this information and/or other information. In respect of prostate cancer, for example, such other information may include serum PSA measurements, DRE and/or ultrasonography. Further, the level of BPC-1 detected in the serum may provide information useful in staging or prognosis. For example, very high levels of BPC-1 protein in serum may suggest a larger and/or more aggressive tumor.

The brain-specific expression of BPC-1 in normal tissues is expected to provide an important advantage of this aspect of the invention, namely, very low to non-existent background levels of circulating BPC-1, resulting in a high correlation between the presence of serum BPC-1 protein and the presence of cancer. This advantage is expected to result from the characteristics of the blood-brain barrier, a system of tight junctions in capillaries of the central nervous system that resists the passage of cells, pathogens and macromolecules into and out of the subarachnoid space. Accordingly, BPC-1 expressed in the brain is not expected to be released into the vascular system. Since no other normal tissue tested has demonstrated significant expression of BPC-1, the presence of serum BPC-1 would strongly suggest the presence of a BPC-1 expressing tumor.

In addition, peripheral blood may be conveniently assayed for the presence of cancer cells, including but not limited to prostate cancer, using RT-PCR to detect BPC-1 expression. The presence of RT-PCR amplifiable BPC-1 mRNA provides an indication of the presence of prostate cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384; Ghossein et al., 1995, J. Clin. Oncol. 13: 1195–2000; Heston et al., 1995, Clin. Chem. 41: 1687–1688). RT-PCR assays are well known in the art.

A related aspect of the invention is directed to predicting susceptibility to developing cancer in an individual. In one embodiment, a method for predicting susceptibility to cancer comprises detecting BPC-1 mRNA or BPC-1 protein in a tissue sample, its presence indicating susceptibility to cancer, wherein the degree of BPC-1 mRNA expression present is proportional to the degree of susceptibility. In a specific embodiment, the presence of BPC-1 in prostate tissue is examined, with the presence of BPC-1 in the sample providing an indication of prostate cancer susceptibility (or the emergence or existence of a prostate tumor). In another specific embodiment, the presence of BPC-1 in bladder tissue is examined, with the presence of BPC-1 in the sample providing an indication of bladder cancer susceptibility (or the emergence or existence of a bladder tumor). In yet another specific embodiment, the presence of BPC-1 in serum is examined, with the presence of BPC-1 providing an indication of susceptibility to (or presence of) a BPC-1 expressing tumor, such as a bladder or prostate tumor. In another embodiment, the presence of BPC-1 in urine is examined, with the presence of BPC-1 therein providing an indication of susceptibility to (or presence of) a BPC-1 expressing bladder tumor.

Yet another related aspect of the invention is directed to methods for gauging tumor aggressiveness. In one embodiment, a method for gauging aggressiveness of a tumor comprises determining the level of BPC-1 mRNA or BPC-1 protein expressed by cells in a sample of the tumor, comparing the level so determined to the level of BPC-1 mRNA or BPC-1 protein expressed in a corresponding normal tissue taken from the same individual or a normal tissue reference sample, wherein the degree of BPC-1 mRNA or BPC-1 protein expression in the tumor sample relative to the normal sample indicates the degree of aggressiveness. In a specific embodiment, aggressiveness of prostate tumors is evaluated by determining the extent to which BPC-1 is expressed in the tumor cells, with higher expression levels indicating more aggressive tumors.

In a related embodiment, serum levels of BPC-1 may be used to provide an indication of the extent and aggressiveness of a BPC-1 expressing tumor, wherein higher levels of serum BPC-1 may suggest a more advanced and more aggressive tumor. Serum BPC-1 measurements over time would be expected to provide further information, wherein an increase in BPC-1 would be expected to reflect progression and the rate of the increase would be expected to correlate with aggressiveness. Similarly, a decline in serum BPC-1 would be expected to reflect a slower growing or regressing tumor. The identification of BPC-1 in serum may be useful to detect tumor initiation and early stage disease, particularly since background BPC-1 interference is expected to be minimal to non-existent in view of the BPC-1 brain specific expression profile in normal individuals. In patients who have undergone surgery or therapy, serum BPC-1 levels would be useful for monitoring treatment response and potential recurrence. As an alternative or adjunct to serum BPC-1 measurements, the presence and levels of BPC-1 secreted in urine may be useful in relation to bladder cancer.

Methods for detecting and quantifying the expression of BPC-1 mRNA or protein are described herein and use standard nucleic acid and protein detection and quantification technologies well known in the art. Standard methods for the detection and quantification of BPC-1 mRNA include in situ hybridization using labeled BPC-1 riboprobes, Northern blot and related techniques using BPC-1 polynucleotide probes, RT-PCR analysis using primers specific for BPC-1, and other amplification type detection methods, such as, for example, branched DNA, SISBA, TMA and the like. In a specific embodiment, semi-quantitative RT-PCR may be used to detect and quantify BPC-1 mRNA expression as described in the Examples which follow. Any number of primers capable of amplifying BPC-1 may be used for this purpose, including but not limited to the various primer sets specifically described herein. Standard methods for the detection and quantification of protein may be used for this purpose. In a specific embodiment, polyclonal or monoclonal antibodies specifically reactive with the wild-type BPC-1 protein may be used in an immunohistochemical assay of biopsied tissue.

ASSAYS FOR CIRCULATING AND EXCRETED BPC-1

The mature BPC-1 is a secreted protein. Tumors which express BPC-1 would be expected to secrete BPC-1 into the vasculature, and/or excreted in urine or semen, where the protein may be detected and quantified using assays and techniques well known in the molecular diagnostic art. Excreted BPC-1 may also be detectable in urine and semen. Detecting and quantifying the levels of circulating or excreted BPC-1 is expected to have a number of uses in the diagnosis, staging, and prognosis of prostate, bladder and other such BPC-1 expressing tumors. A number of different technical approaches for the detection and quantification of serum proteins are well known in the art.

Detecting BPC-1 protein in urine may indicate the presence of a bladder cancer secreting BPC-1. Normally, significant levels of protein are not detected in urine, provided that renal function is normal. However, proteins expressed and secreted by bladder cancer cells may enter urine in the bladder directly, permitting their detection in urine. Interestingly, the BPC-1 protein exhibits a relatively high degree of stability in recombinant cell culture media, suggesting that the protein may also remain stable in urine.

In one embodiment, a capture ELISA is used to detect and quantify BPC-1 in serum, urine or semen. A capture ELISA for BPC-1 comprises, generally, at least two monoclonal antibodies of different isotypes that recognize distinct epitopes of the BPC-1 protein, or one anti-BPC-1 monoclonal antibody and a specific polyclonal serum derived from a different species (e.g., rabbit, goat, sheep, hamster, etc.). In this assay, one reagent serves as the capture (or coating) antibody and the other as the detection antibody (see Example 13 herein).

THERAPEUTIC METHODS AND COMPOSITIONS

The identification of BPC-1 as a secreted protein which is only expressed in tissues of the brain in normal individuals but which is highly expressed in prostate cancer (as well as expressed in bladder carcinoma and possibly other cancers), opens a number of therapeutic approaches to the treatment of prostate, bladder and potentially other cancers. Applicants' initial functional research suggests that BPC-1 has transformation activity and that this activity is initiated through the interaction of BPC-1 to a cellular protein, or through binding to or association with another protein. The protein's CUB domain may also function as a protein-protein interaction domain, mediating interactions with other secreted molecules, extracellular matrix molecules and/or cell surface receptors.

Accordingly, therapeutic approaches aimed at inhibiting the activity of the BPC-1 protein are expected to be useful for patients suffering from prostate cancer, bladder cancer, and other cancers expressing BPC-1. These therapeutic approaches generally fall into two classes. One class comprises various methods for inhibiting the binding of the BPC-1 protein to its receptor, or inhibiting its binding to or association with another protein. Another class comprises a variety of methods for inhibiting the transcription of the BPC-1 gene or translation of BPC-1 mRNA.

A. Therapeutic Methods Based on Inhibition of BPC-1 Protein Function

Within the first class of therapeutic approaches, the invention includes various methods and compositions for inhibiting the binding of BPC-1 to its receptor or other binding partner or its association with other protein(s) as well as methods for inhibiting BPC-1 function.

A.1. Therapeutic Inhibition of BPC-1 with BPC-1 Antibodies

In one approach, antibodies which bind to BPC-1 and thereby inhibit the ability of BPC-1 to bind to its coordinate binding partner, or to bind to or associate with other protein(s), may be used to attenuate an oncogenic/transformation signal pathway involving BPC-1. To the extent BPC-1 is involved in initiating, promoting and/or sustaining tumor cell growth or other tumor cell properties through a binding partner-mediated signal, such antibodies are expected to be therapeutically useful.

BPC-1 antibodies and fragments thereof which are capable of inhibiting BPC-1 function are expected to be useful in treating prostate, bladder, and possibly other cancers. Such antibodies may function to inhibit BPC-1 activity in different ways. For example, a BPC-1 antibody may prevent BPC-1 binding to its receptor or binding to/associating with another protein.

Alternatively, a BPC-1 antibody may bind to a biologically active domain of the BPC-1 protein, thereby inhibiting function. In this regard, antibodies specifically directed to the BPC-1 CUB domain (see FIG. 1) may be particularly effective in either inhibiting BPC-1 binding (if the CUB domain is functionally involved in binding) or in otherwise inhibiting the CUB domain's function. Such domain-specific BPC-1 antibodies may be generated as previously described. For example, the CUB domain amino acid sequence shown in FIG. 1 may be used to generate a CUB-domain immunogen for the generation of such antibodies.

With respect to the treatment of cancer with BPC-1 antibodies, a number of factors may be considered, including but not limited to the following. First, monoclonal antibodies are generally preferred, particularly those with very high binding affinity for the secreted BPC-1 protein. Second, fully human or humanized monoclonal antibodies exhibiting low or no antigenicity in the patient are preferred. The use of murine or other non-human monoclonal antibodies and human/mouse chimeric mAbs may induce moderate to strong immune responses in some patients. Third, the method by which the antibodies are delivered to the patient may vary with the type of cancer being treated.

Generally, where the therapeutic objective is the inhibition of BPC-1 activity or signal transduction in the target tumor tissue, administration of BPC-1 antibodies directly to the tumor site may provide local elimination of BPC-1 function sufficient to generate a clinical response. Direct administration of BPC-1 Mabs is also possible and may have advantages in certain contexts. For example, for the treatment of bladder carcinoma, BPC-1 Mabs may be injected directly into the bladder.

Alternatively, BPC-1 antibodies may be administered systemically, which may result in elimination of BPC-1 function in the primary tumor, in circulating micrometastasis, and/or in established metastasis. The degree of tumor vascularization may provide guidance on which delivery approach is recommended. Similarly, the grade and/or stage of disease would be expected to provide useful information in this regard. For example, a higher grade, more advanced tumor may be more likely to seed metastasis, suggesting systemic administration in order to treat or prevent the emergence of metastases.

BPC-1 mAbs may be therapeutically useful either alone or as well as combinations, or "cocktails", of different mAbs such as those recognizing different epitopes. Such mAb cocktails may have certain advantages inasmuch as they contain mAbs which bind to different epitopes and enhance the functional inhibition of BPC-1. In addition, the administration of BPC-1 mAbs may be combined with other therapeutic agents, including but not limited to various chemotherapeutic agents, androgen-blockers, and immune modulators (e.g., IL-2, GM-CSF).

Treatment of cancer with a BPC-1 antibody will generally involve the administration of the BPC-1 antibody preparation via an acceptable route of administration such as intravenous injection (IV) or bolus infusion, typically at a dose in the range of about 0.1 to about 200 mg/kg body weight. Doses in the range of 10–500 mg mAb per week (or more) may be effective and well tolerated. An initial loading dose followed by smaller weekly doses of the mAb preparation may be used. As one of skill in the art will understand, various factors will influence the ideal dose regimen in a particular case. Such factors may include, for example, the binding affinity and half life of the mAb or mAbs used, the degree of BPG-1 expression in the patient, the desired steady-state antibody concentration level, frequency of treatment, and the influence of chemotherapeutic agents or other therapies used in combination with the therapeutic composition.

A.2. Therapeutic Inhibition of BPC-1 with Intracellular Antibodies

In another approach, recombinant vectors encoding single chain antibodies which specifically bind to BPC-1 may be introduced into BPC-1 expressing cells via gene transfer technologies, wherein the encoded single chain anti-BPC-1 antibody is expressed intracellularly, binds to BPC-1 protein, and thereby inhibits its function. Methods for engineering such intracellular single chain antibodies are well known. Such intracellular antibodies, also known as "intrabodies", may be specifically targeted to a particular compartment within the cell, providing a great deal of control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337.

Single chain antibodies comprise the variable domains of the heavy and light chain joined by a flexible linker polypeptide, and is expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, intrabodies may be used to capture BPC-1 in the ER, thereby preventing its maturation and secretion outside of the cell. ER-targeting signals and/or leader peptides may be engineered into such BPC-1 intrabodies in order to achieve the desired targeting. Such intrabodies would be expected to capture BPC-1 as its is being processed by the ER, thereby inhibiting BPC-1 processing or transport through the plasma membrane of the cell. This method would essentially prevent the existence of secreted mature bioactive BPC-1 at the level of the ER. Such BPC-1 intrabodies may be designed to bind specifically to a particular BPC-1 domain, including the signal sequence of precursor BPC-1. Endoplasmic reticulum-targeted intrabodies reactive with the BPC-1 protein would be expected to capture BPC-1 in the endoplasmic reticulum. In another embodiment, intrabodies specifically reactive with the BPC-1 CUB domain may be used to block BPC-1 CUB domain function within the cytosol.

A.3. Therapeutic Inhibition of BPC-1 with Recombinant Proteins

In another approach, recombinant molecules which are capable of binding to BPC-1 thereby preventing BPC-1 from accessing/binding to its coordinate receptor or associating with another protein involved in transmitting an oncogenic signal may be used to inhibit BPC-1 function. Such recombinant molecules may, for example, contain the reactive part(s) of a BPC-1 specific antibody molecule. In a particular embodiment, the BPC-1 ligand binding domain of a BPC-1 receptor or binding partner may be engineered into a dimeric fusion protein comprising two BPC-1 ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of BPC-1, including but not limited to prostate and bladder cancers, where the dimeric fusion protein specifically binds to BPC-1 thereby blocking BPC-1 interaction with its receptor or other binding partner. Such dimeric fusion proteins may be further combined into multimeric proteins using known antibody linking technologies.

B. Therapeutic Methods Based on Inhibition of BPC-1 Transcription or Translation Within the second class of therapeutic approaches, the invention provides various methods and compositions for inhibiting the transcription of the BPC-1 gene. Similarly, the invention also provides methods and compositions for inhibiting the translation of BPC-1 mRNA into protein.

In one approach, a method of inhibiting the transcription of the BPC-1 gene comprises contacting the BPC-1 gene with a BPC-1 antisense polynucleotide. In another approach, a method of inhibiting BPC-1 mRNA translation comprises contacting the BPC-1 mRNA with an antisense polynucleotide. In another approach, a BPC-1 specific ribozyme may be used to cleave the BPC-1 message, thereby inhibiting translation. Such antisense and ribozyme based methods may also be directed to the regulatory regions of the BPC-1 gene, such as the BPC-1 promoter and/or enhancer elements. Similarly, proteins capable of inhibiting a BPC-1 gene transcription factor may be used to inhibit BPC-1 mRNA transcription. The various polynucleotides and compositions useful in the aforementioned methods have been described above. The use of antisense and ribozyme molecules to inhibit transcription and translation is well known in the art.

The 5' untranslated region (UTR) of the BPC-1 cDNA of FIG. 1 is an extremely GC rich sequence, strongly implying the presence of translational control elements within this part of the BPC-1 mRNA. This characteristic of the BPC-1 gene suggests that blocking accessibility of the 5' UTR may result in inhibition of BPC-1 translation. In one approach, an antisense molecule complementary to the 5' UTR of the BPC-1 mRNA is contacted with the 5' UTR of the BPC-1 message, thereby resulting in hybridization which prevents endogenous BPC-1 translation factors from accessing the necessary activation element(s) in the BPC-1 5' UTR. A modification of this approach uses an polynucleotide comprising a sequence complementary to the 5' UTR BPC-1 mRNA joined to a ribozyme or similarly active polynucleotide capable of splicing the BPC-1 mRNA, thereby adding a second layer of translational inhibition.

Although, in the above method, a BPC-1 splicing ribozyme may be contacted with the BPC-1 mRNA separately, i.e., not joined to a heterologous sequence such as the anti-5' UTR mentioned above, delivering the ribozyme or similarly active polynucleotide as part of such a heterologous BPC-1 hybridizing polynucleotide would be expected to result in placing the ribozyme in direct proximity to the target sequence and may result in a higher level of inhibitory activity.

Other factors which inhibit the transcription of BPC-1 through interfering with BPC-1 transcriptional activation may also be useful for the treatment of cancers expressing BPC-1, and cancer treatment methods utilizing such factors are also within the scope of the invention. Similarly, factors which are capable of interfering with BPC-1 processing may be useful for the treatment of cancers expressing BPC-1.

C. General Considerations

Gene transfer and gene therapy technologies may be used for delivering therapeutic polynucleotide molecules to tumor cells synthesizing BPC-1 (i.e., antisense, ribozyme, polynucleotides encoding intrabodies and other BPC-1 inhibitory molecules). A number of gene therapy approaches are known in the art. Recombinant vectors encoding BPC-1 antisense polynucleotides, ribozymes, factors capable of interfering with BPC-1 transcription, factors which are capable of interfering with processing and/or secretion of mature BPC-1, and so forth, may be delivered to target tumor cells using such gene therapy approaches.

The above therapeutic approaches may be combined with chemotherapy or radiation therapy regimens. These therapeutic approaches may also enable the use of reduced dosages of concomitant chemotherapy, particularly in patients that do not tolerate the toxicity of the chemotherapeutic agent well.

The anti-tumor activity of a particular composition (e.g., antibody, ribozyme, recombinant fusion protein), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of BPC-1 to its coordinate receptor or other binding partner, cell adhesion assays, and the like. For example, antibody to HER2 inhibits binding of ligand to receptor and leads to the inhibition of tumor growth. Additionally, for example, antibodies to EGFR inhibit binding of EGF to receptor, leading to growth arrest and tumor inhibition. See, also, the Examples below.

Various in vitro assays for determining binding affinity of the therapeutic composition for its target are also known. For example, binding affinities of BPC-1 antibodies may be determined using a number of techniques well known in the art (e.g., BIAcore technology). Higher affinity BPC-1 antibodies are expected to provide greater levels of the desired inhibition and are therefore preferred.

In vivo, the effect of a BPC-1 therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402–408). For Example, PCT Patent Application WO98116628, Sawyers et al., published Apr. 23, 1998, describes various xenograft models of human prostate cancer capable of recapitulating the development of primary tumors, micrometastasis, and the formation of osteoblastic metastases characteristic of late stage disease. Various bladder carcinoma models are known (see, for example, Russell et al., 1986, Cancer Res. 46: 2035–2040; Raghavan et al., 1992, Semin. Surg. Oncol. 8: 279–284; Rieger et al., 1995, Br. J. Cancer 72: 683–690; Oshinsky et al., 1995, J. Urol. 154: 1925–1929). Efficacy may be predicted using assays which measure inhibition of tumor formation, tumor regression or metastasis, and the like. See, also, the Examples below.

In vivo assays which qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice would provide an indication of the therapeutic efficacy of the composition.

The therapeutic compositions used in the practice of the foregoing methods may be formulated into pharmaceutical compositions comprising a carrier suitable for the desired delivery method. Suitable carriers include any material which when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition (i.e., BPC-1 monoclonal antibody) in a solution of preserved bacteriostatic water, sterile unpreserved water, and/or diluted in polyvinylchloride or polyethylene bags containing 0.9% sterile Sodium Chloride for Injection, USP. The anti-BPC-1 mAb preparation may be lyophilized and stored as a sterile powder, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

The invention further provides prostate cancer vaccines comprising a BPC-1 protein or fragment thereof. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231–237; Fong et al., 1997, J. Immunol. 159: 3113–3117). Such methods can be readily practiced by employing a BPC-1 protein, or fragment thereof, or a BPC-1-encoding nucleic acid molecule and recombinant vectors capable of expressing and appropriately presenting the BPC-1 immunogen.

For example, viral gene delivery systems may be used to deliver a BPC-1-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a BPC-1 protein or fragment thereof introduced into the patient (e.g., intramuscularly) to induce an anti-tumor response. In one embodiment, the full-length human BPC-1 cDNA may be employed. In another embodiment, BPC-1 nucleic acid molecules encoding specific cytotoxic T lymphocyte (CTL) epitopes may be employed. CTL epitopes can be determined using specific algorithms (e.g., Epimer, Brown University) to identify peptides within a BPC-1 protein which are capable of optimally binding to specified HLA alleles.

Various ex vivo strategies may also be employed. One approach involves the use of dendritic cells to present BPC-1 antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65–69; Murphy et al., 1996, Prostate 29: 371–380). Dendritic cells can be used to present BPC-1 peptides to T cells in the context of MHC class I and II molecules. In one embodiment, autologous dendritic cells are pulsed with BPC-1 peptides capable of binding to MHC molecules. In another embodiment, dendritic cells are pulsed with the complete BPC-1 protein. Yet another embodiment involves engineering the overexpression of the BPC-1 gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182). Cells expressing BPC-1 may also be engineered to express immune modulators, such as GM-CSF, and used as immunizing agents.

Anti-idiotypic anti-BPC-1 antibodies can also be used in anti-cancer therapy as a vaccine for inducing an immune response to cells expressing a BPC-1 protein. Specifically, the generation of anti-idiotypic antibodies is well known in the art and can readily be adapted to generate anti-idiotypic anti-BPC-1 antibodies that mimic an epitope on a BPC-1 protein (see, for example, Wagner et al., 1997, Hybridoma 16: 33–40; Foon et al., 1995, J Clin Invest 96: 334–342; Herlyn et al., 1996, Cancer Immunol Immunother 43:

65–76). Such an anti-idiotypic antibody can be used in cancer vaccine strategies.

Genetic immunization methods may be employed to generate prophylactic or therapeutic humoral and cellular immune responses directed against cancer cells expressing BPC-1. Constructs comprising DNA encoding a BPC-1 protein/immunogen and appropriate regulatory sequences may be injected directly into muscle or skin of an individual, such that the cells of the muscle or skin take-up the construct and express the encoded BPC-1 protein/immunogen. Expression of the BPC-1 protein immunogen results in the generation of prophylactic or therapeutic humoral and cellular immunity against prostate cancer. Various prophylactic and therapeutic genetic immunization techniques known in the art may be used (for review, see information and references published at Internet address www.genweb.com).

KITS

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe which is or can be detectably labeled. Such probe may be an antibody or polynucleotide specific for a BPC-1 protein or a BPC-1 gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

EXAMPLES

Various aspects of the invention are further described and illustrated by way of the several examples which follow, none of which are intended to limit the scope of the invention.

Example 1

Isolation of cDNA Fragment of BPC-1 Gene

Materials and Methods

LAPC Xenografts:

LAPC xenografts were obtained from Dr. Charles Sawyers (UCLA) and generated as described (Klein et al, 1997, Nature Med. 3: 402–408). Androgen dependent and independent LAPC-4 xenografts LAPC-4 AD and AI, respectively) and LAPC-9 AD xenografts were grown in male SCID mice and were passaged as small tissue chunks in recipient males. LAPC-4 AI xenografts were derived from LAPC-4 AD tumors. Male mice bearing LAPC-4 AD tumors were castrated and maintained for 2–3 months. After the LAPC-4 tumors re-grew, the tumors were harvested and passaged in castrated males or in female SCID mice.

Cell Lines:

Human cell lines (e.g., HeLa) were obtained from the ATCC and were maintained in DMEM with 10% fetal calf serum.

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
5'TTTTGATCAAGCTT₃₀3'                         (SEQ ID NO. 9)
Adaptor 1:
                                             (SEQ ID NO. 10)
5'CTAATACGACTCACTATAGGGCTCGAGCGGCCGCCCGGGCAG3'
                            3'GGCCCGTCCTAG5'

Adaptor 2:
                                             (SEQ ID NO. 11)
5'GTAATACGACTCACTATAGGGCAGCGTGGTCGCGGCCGAG3'
                            3'CGGCTCCTAG5'

PCR primer 1:
5'CTAATACGACTCACTATAGGGC3'                   (SEQ ID NO. 12)

Nested primer (NP)1:
5'TCGAGCGGCCGCCCGGGCAGGA3'                   (SEQ ID NO. 13)
Nested primer (NP)2:
5'AGCGTGGTCGCGGCCGAGGA3'                     (SEQ ID NO. 14)
```

Suppression Subtractive Hybridization:

Suppression Subtractive Hybridization (SSH) was used to identify cDNAs corresponding to genes which may be down-regulated in androgen independent prostate cancer compared to androgen dependent prostate cancer.

Double stranded cDNAs corresponding to the LAPC-4 AD xenograft (tester) and the LAPC-4 AI xenograft (driver) were synthesized from 2 μg of poly(A)$^+$ RNA isolated from xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA (LAPC-4 AI) was generated by combining in a 1:1 ratio Dpn II digested LAPC-4 AI cDNA with a mix of digested cDNAs derived from human benign prostatic hyperplasia (BPH), the human cell lines HeLA, 293, A431, Colo205, and mouse liver.

Tester cDNA (LAPC-4 AD) was generated by diluting 1 μl of Dpn II digested LAPC-4 AD cDNA (400 ng) in 5 μl of water. The diluted cDNA (2 μl, 160 ng) was then ligated to 2 μl of adaptor 1 and adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) adaptor 1- and adaptor 2-ligated tester cDNA. In a final volume of 4 μl, the samples were overlayed with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10×reaction buffer (CLONTECH) and 0.5 μl 50×Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10–12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs were generated from 1 μg of mRNA with oligo (dT)12–18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 μl with water prior to normalization. First strand cDNAs from 16 different normal human tissues were obtained from Clontech.

Normalization of the first strand cDNAs from multiple tissues was performed by using the primers 5'atatcgccgcgctcgtcgtcgacaa3' and 5'agccacacgcagctcattgtagaagg 3' to amplify β-actin. First strand cDNA (5 μl) was amplified in a total volume of 50 μl containing 0.4 μM primers, 0.2 μM each dNTPs, 1×PCR buffer (Clontech, 10 mM Tris-HCL, 1.5 mM $MgCl_2$, 50 mM KCl, pH8.3) and 1×Klentaq DNA polymerase (Clontech). Five μl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 19P1E8 gene, 5 μl of normalized first strand cDNA was analyzed by PCR using 25, 30, and 35 cycles of amplification using the following primer pairs, which were designed with the assistance of (MIT; for details, see, www.genome.wi.mit.edu):

5'-TGC CGT ATG TCA CTG TCT CTA GGT-3' (SEQ ID NO. 15)

5'-GAA ATC ATG GGT ATT TCA TGT GCT-3' (SEQ ID NO. 16)

These primers were designed from the sequence of the SSH fragment of the initially isolated 19P1E8 gene. Use of the following primer pair, based on sequences within the open reading frame of the 19P1E8 gene, produced the same expression pattern.

5'-CTC CCA ACT ATC CCA GCA AGT ATC-3' (SEQ ID NO. 17)

5'-AAA TCC CAT AGA TTC CAG CTC TCC-3' (SEQ ID NO. 18)

Semi quantitative expression analysis was achieved by comparing the PCR products at cycle numbers that give light band intensities.

RESULTS:

Several SSH experiments were conduced as described in the Materials and Methods, supra, and led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

Figure 9:
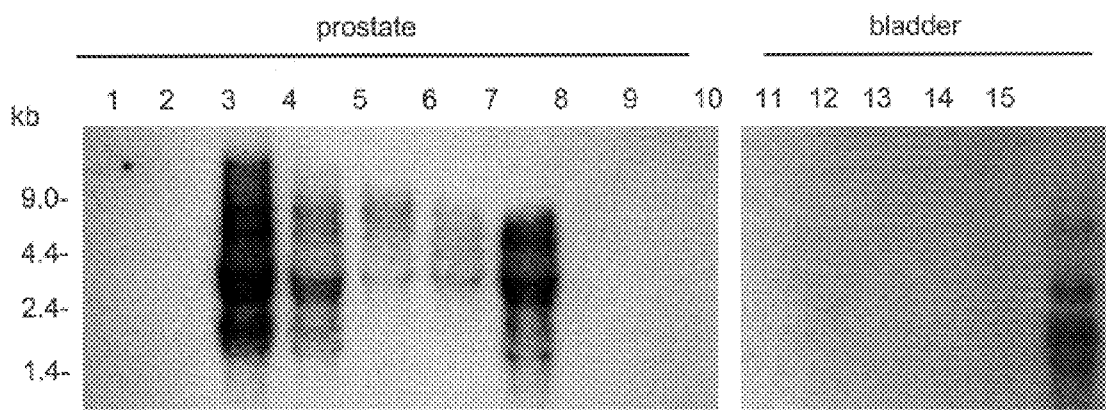
FIG. 9. Northern blot analysis of human BPC-1 mRNA expression in a panel of prostate and bladder carcinoma xenografts and/or cell lines, showing expression in all prostate cancer xenograft samples, the LnCAP prostate cancer cell line, and a bladder carcinoma cell line.

One of the SSH clones comprising about 700 bp, showed no homology to any known gene or EST sequence was designated 19P1E8. The nucleotide sequence of this SHH clone is shown in FIG. 1, approximately nucleotide residues 1883–2583. Differential expression analysis by Northern blot showed that 19P1E8 is expressed in LAPC-4 AD xenograft, and to a significantly lesser extent in LAPC-4 AI, LAPC-9 AD and LAPC-9 AI (FIG. 9). No expression was detected in normal prostate (FIG. 9). Three distinct transcripts are shown, with sizes of 3.5 kb, 8 kb, and greater than 9 kb.

RT-PCR analysis of 19P1E8 expression produced essentially identical results (FIG. 5, Panel A). In addition, further RT-PCR expression analysis of first strand cDNAs from 16 normal tissues detected expression of the 19P1E8 gene only in brain, spleen and testis tissue, and only at very low levels detectable at 35 and not 30 cycles of PCR amplification (FIG. 5, panels B and C). In comparison, substantial expression was detected in LAPC-4 AD with only 30 cycles (FIG. 5).

Example 2

Isolation of Full Length BPC-1 Encoding cDNA

The 19P1E8 SHH clone above (Example 1) was used to isolate a full length 19P1E8 cDNA. Briefly, a cDNA library generated from LAPC-4 mRNA was screened with a labeled probe generated from the SSH clone. Specifically, a full length 19P1E8 cDNA of 2639 base pairs (bp) was cloned from an LAPC-4 AD cDNA library generated in lambda ZAP Express (Stratagene).

The cDNA encodes an open reading frame (ORF) of 158 amino acids containing a signal sequence and a CUB domain (Complement sub-components C1r/C1s, Uegf, Bmp1) (Borck and Beckmann, 1993, J. Mol. Biol. 231: 539–545). The 5' UTR (untranslated region) is very GC rich, suggesting that this region contains regulatory elements for translation. CUB domains were originally found in complement sub-components CIr and CIs, and were subsequently identified in Uegf (epidermal growth factor related sea urchin protein) and Bmp1 (bone morphogenetic protein 1) a protease involved in bone development.

In view of the exclusive expression of this gene in brain and its up-regulation in prostate cancer xenografts, this gene was named BPC-1 (Brain/Prostate cancer CUB protein). The nucleotide and deduced amino acid sequences of the isolated BPC-1 cDNA are shown in FIG. 1. A schematic representation of the BPC-1 structure is shown in FIG. 2. An amino acid alignment between the CUB domain of BPC-1 and the CUB domains of other proteins is shown in FIG. 3. Referring to FIG. 3, of particular interest is that the CUB domain of BPC-1 is 30–40% identical to the CUB domains in BMP-1.

The full length BPC-1 cDNA (p19P1E8, clone 6.1) was deposited with the American Type Culture Collection, 10801 University Boulevard, Manassas, Va. 20110-2209, on Aug. 7, 1998 and has been accorded ATCC accession number 98833.

Example 3

BPC-1 Gene Expression Analysis—Brain Specific in Normal Tissues

Initial analysis of BPC-1 mRNA expression in normal human tissues was conducted by Northern blotting two multiple tissue blots obtained from Clontech (Palo Alto, Calif.), comprising a total of 16 different normal human tissues, using labeled 19P1E8 SSH clone (Example 1) as a probe. RNA samples were quantitatively normalized with a β-actin probe.

The results are shown in FIG. 4. Expression was only detected in normal brain. The northern blots showed two transcripts of 3.5 kb and 8.0 kb (FIG. 5). The 3.5 kb transcript corresponds to the cDNA identified from LAPC-4 AD that encodes the BPC-1 ORF. The larger transcript may encode an un-processed message or an alternative isoform of the gene.

Figure 7:
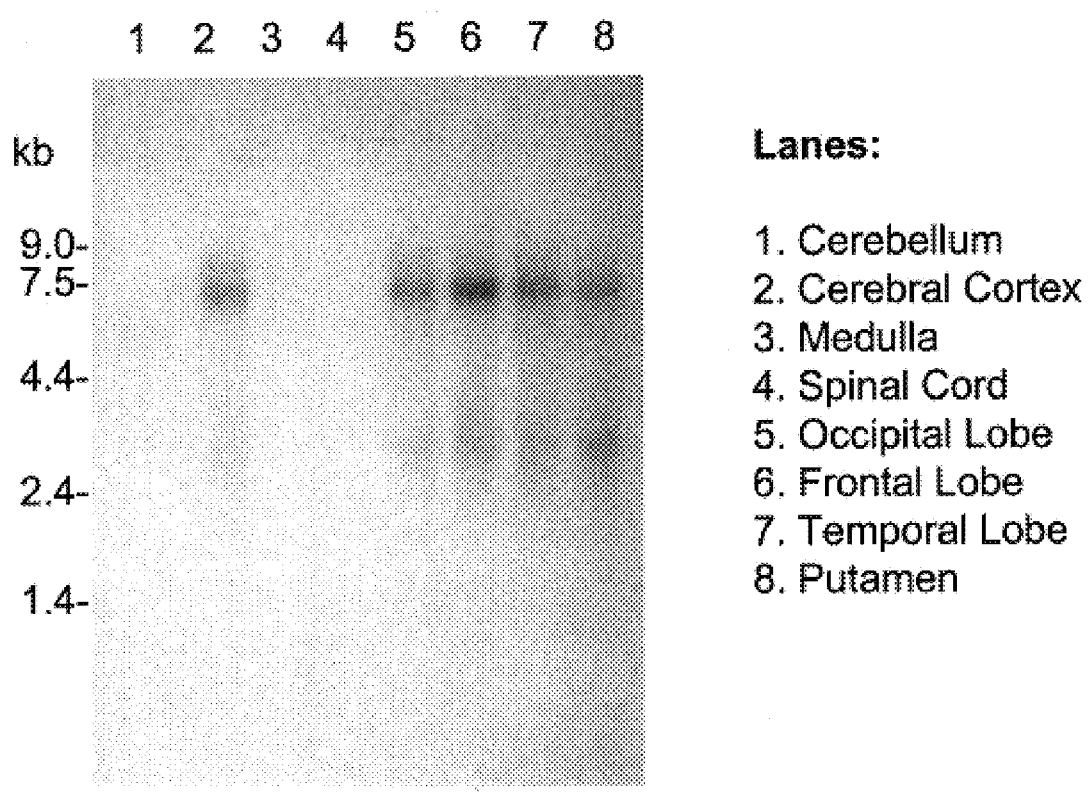
FIG. 7. Northern blot analysis of human BPC-1 mRNA expression in cortical regions of the brain, showing expression only in specific regions of the cortex.

To further explore BPC-1 expression in normal tissues, a multi-tissue RNA dot blot was probed with a BPC-1 probe. Out of 37 different normal tissues tested, only brain regions exhibited detectable levels of BPC-1 (FIG. 6). Interestingly, expression of BPC-1 was confined to cortical regions of the brain, such as the temporal, frontal and occipital lobes. Expression was also seen in hippocampus, amygdala, caudate nucleus and putamen. Other brain regions such as thalamus, sub-thalamic nucleus and substantia nigra did not express BPC-1. Similarly, no expression was detected in other central nervous system (CNS) structures such as cerebellum, spinal cord and medulla oblongata (mid-brain). The RNA dot blot results were confirmed with a northern blot containing RNA for different CNS tissues (FIG. 7).

Example 4

BPC-1 Expression in Fetal Tissues—Broader Expression in Development

Figure 8:
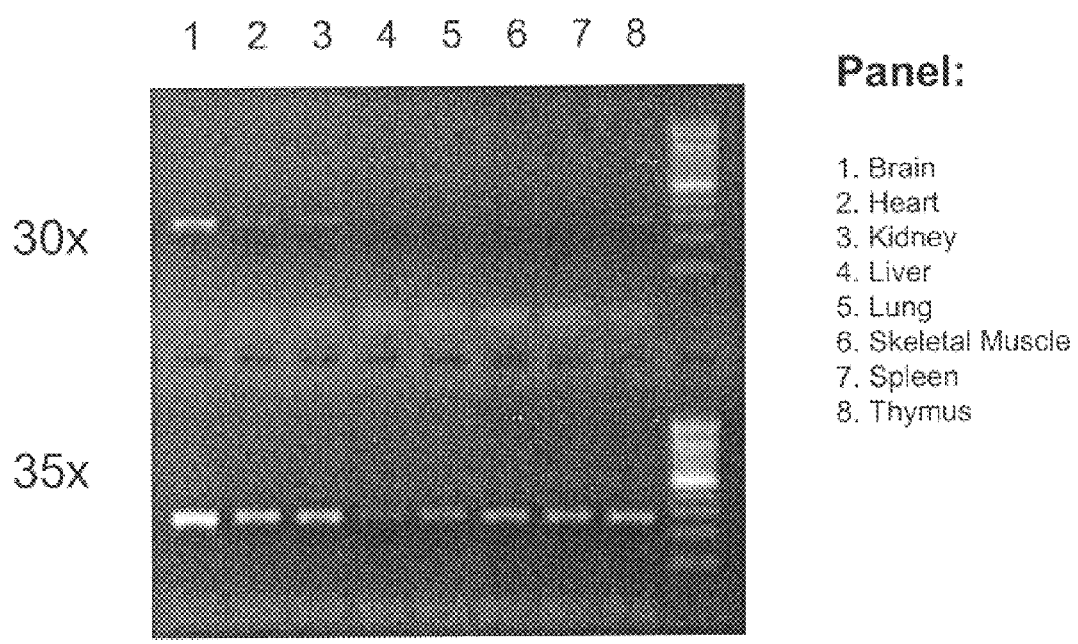
FIG. 8. Semi-quantitative RT-PCR expression analysis of human BPC-1 expression in fetal tissues, showing that BPC-1 expression is predominant in fetal brain, and is also expressed at lower levels in a number of other fetal tissues.

CUB domain proteins often are often developmentally regulated. To determine if BPC-1 is expressed in human fetal tissue, RT-PCR was performed on first strand cDNA derived from 8 different fetal tissues. The results show that BPC-1 is highly expressed in fetal brain, with lower levels detected in all other fetal tissues (FIG. 8). This suggests that expression in the adult is exclusive to brain, while expression in other tissues is turned off during development.

Example 5

High Level BPC-1 Expression in Prostate Cancer

To analyze BPC-1 expression in cancer tissues and cell lines, Northern blot analysis was performed on RNA derived from the LAPC prostate cancer xenografts as well as a panel of prostate and bladder cancer cell lines. The results, shown in FIG. 9, reveal the highest levels of BPC-1 expression in the LAPC-4 AD prostate cancer xenograft and in the LNCaP prostate cancer cell line, both of which originated from lymph-node metastasis of prostate cancer (Klein et a., 1997, Nature Med. 3:402; Horoszewicz et al., 1983, Cancer Res. 43:1809). Lower level expression of BPC-1 was detected in LAPC-4 AI, LAPC-9 AD and LAPC-9 AI (FIG. 9). Among the bladder cancer cell lines tested, one (5637) showed detectable BPC-1 expression (FIG. 9). No expression was detected in PrEC cells (Clonetics), which represent the basal cell compartment of the prostate and normal prostate.

Example 6

Production of Secreted Recombinant BPC-1 in Vitro

To express recombinant BPC-1 and analyze the subcellular localization of BPC-1 protein, the full length cDNA was cloned into an expression vector that provides a 6His tag at the carboxyl-terminus (pCDNA 3.1 myc-his, InVitrogen). The construct was transfected into 293T cells which were labeled for one hour with $^{35}$S-methionine. The cells were then washed and incubated in non-radioactive media to chase the labeled proteins for various time points. BPC-1-His tagged protein was immunoprecipitated using anti-His antibodies (Santa Cruz) from cell extracts and from cell supernatant (media) at various time points after the chase. The immunoprecipitates were analyzed by SDS-PAGE (sodium-dodecyl sulfate polyacrylamide-gel electrophoresis) with subsequent autoradiography to visualize $^{35}$S-methionine labeled protein.

Figure 10:
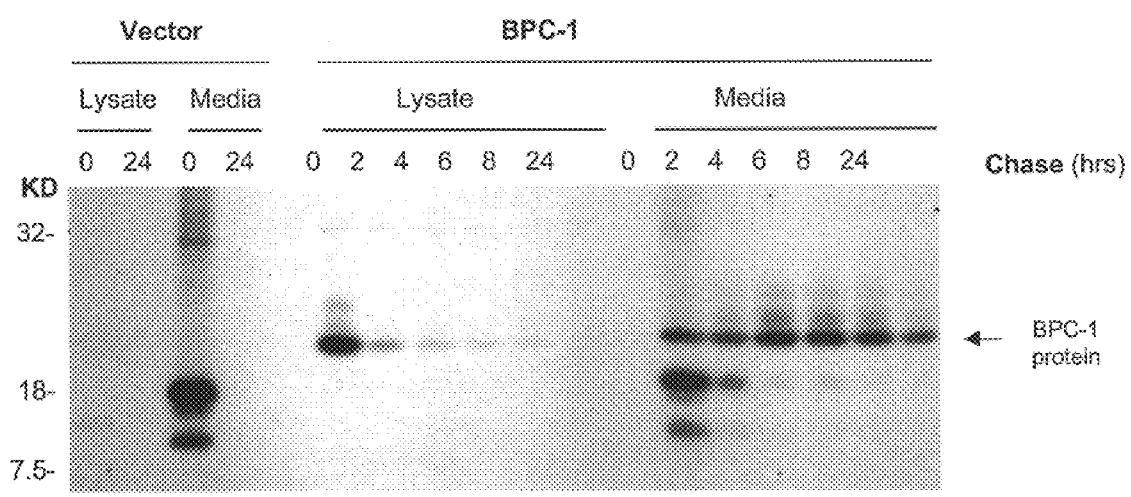
FIG. 10. SDS-PAGE autoradiography of immunoprecipitated recombinant human BPC-1 protein secreted into the tissue culture media of BPC-1 transfected 293T cells.

The results show that BPC-1 protein appears in the cell extract and the cell media immediately after the $^{35}$S-methionine labeling period (FIG. 10). Within two hours of the chase, nearly all BPC-1 protein is secreted into the media and remains stable in the media for several hours. The half-life of the protein is estimated to be longer than 24 hours. Vector transfected cells were also labeled and analyzed using the same protocol. Interestingly, a non-specific protein appears in both the vector and the BPC-1 transfected cells. This protein seems to have a very short half-life in the media compared to BPC-1, as it disappears after the 4 hour time point. These results demonstrate that BPC-1 is indeed a secreted protein that appears to be very stable in cell culture media.

Example 7

Production of Recombinant BPC-1 Using Baculovirus System

To generate recombinant BPC-1 protein in a baculovirus expression system, BPC-1 cDNA was cloned into the baculovirus transfer vector pMelBac (Invitrogen) which provides the honeybee mellitin signal sequence for secretion into the media of insect cells. pMelBac-BPC-1 was co-transfected with helper plasmid pBlueBac4.5 (Invitrogen) into SF9

(Spodoptera frugiperda) insect cells to generate recombinant baculovirus (see Invitrogen instruction manual for details). Baculovirus was collected from cell supernatant and was purified by plaque assay.

Figure 11:
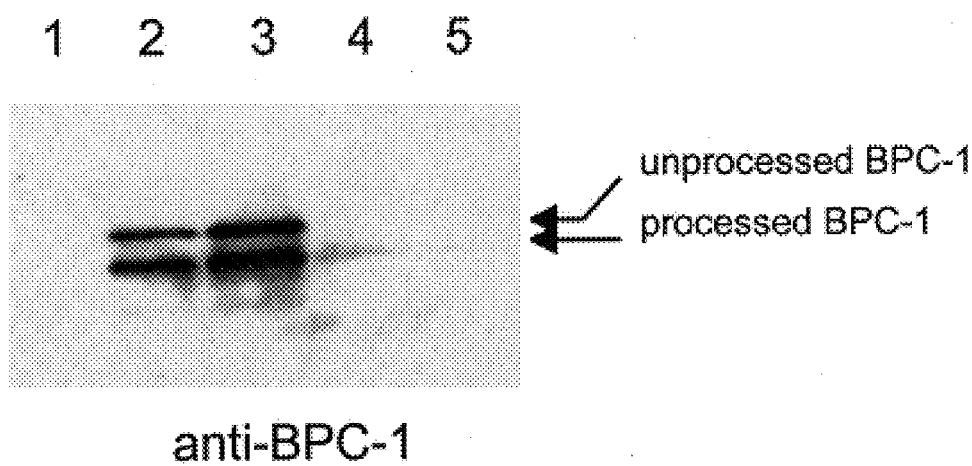
FIG. 11. Western blot analysis of recombinant human BPC-1 protein, as expressed in HighFive insect cells infected with a BPC-1 encoding baculovirus, showing processed mature BPC-1 and unprocessed precursor BPC-1 in cell lysates and low levels of processed mature BPC-1 in cell media.

Recombinant BPC-1 protein was generated by infection of HighFive insect cells (InVitrogen) with purified baculovirus. Recombinant BPC-1 protein was detected in both cell extract and cell supernatant using anti-BPC-1 mouse polyclonal antibody (see Example 8, below). Interestingly, the cell extract contains two forms of BPC-1, signal sequence cleaved BPC-1 and unprocessed BPC-1 (FIG. 11). The supernatant only contained cleaved mature BPC-1. This recombinant BPC-1 protein may be purified and used in various cell based assays or as immunogen to generate polyclonal and monoclonal antibodies specific for BPC-1.

Example 8

Generation of BPC-1 Polyclonal Antibodies

In order to generate antibody reagents that specifically bind to BPC-1, a glutathione-S-transferase (GST) fusion protein encompassing amino acids 29–93 of the BPC-1 protein was synthesized to serve as immunogen. This fusion protein was generated by PCR-mediated amplification of nucleotides 877–1,071 (AA 29–93) of the cDNA clone of BPC-1 with the following primers:

```
                                         (SEQ ID NO:17)
5'PRIMER  TTGAATTCCAAGCAAACCACCTCAGA
          EcoRI (SEQ ID NO:18)
3'PRIMER  AAGCTCGAGTCAGACGGTTCAATAGAGT
          XhoI
```

The resultant product was cloned into the EcoR1 and XhoI restriction sites of the pGEX-2T GST-fusion vector (Pharmacia). Recombinant GST-BPC-1 fusion protein was purified to greater than 90% purity from induced bacteria by glutathione-sepaharose affinity chromatography.

To generate polyclonal sera to BPC-1, the purified fusion protein was used as follows. A rabbit was initially immunized with 200 μg of GST-BPC-1 fusion protein mixed in complete Freund's adjuvant. The rabbit was injected every two weeks with 200 μg of GST-BPC-1 protein in incomplete Freund's adjuvant. Test bleeds were taken approximately 7–10 days following each immunization. ELISA, Western blotting and immunoprecipitation analyses were used to determine specificity and titer of the rabbit serum to BPC-1. Cell lines that express BPC-1 endogenously such as LNCaP and cell lines engineered to overexpress BPC-1 by transfection (293T) and by retroviral infection (PC-3 and NIH3T3) were used for characterization of the antiserum. Antiserum representing specific high titer to BPC-1 protein is purified by a 3 step process: (1) removal of GST-reacUve antibody by depletion over a GST affinity column, (2) BPC-1 specific IgG antibody was isolated by passage over a GST-BPC-1 affinity column, and (3) protein G chromatography.

Figure 13:
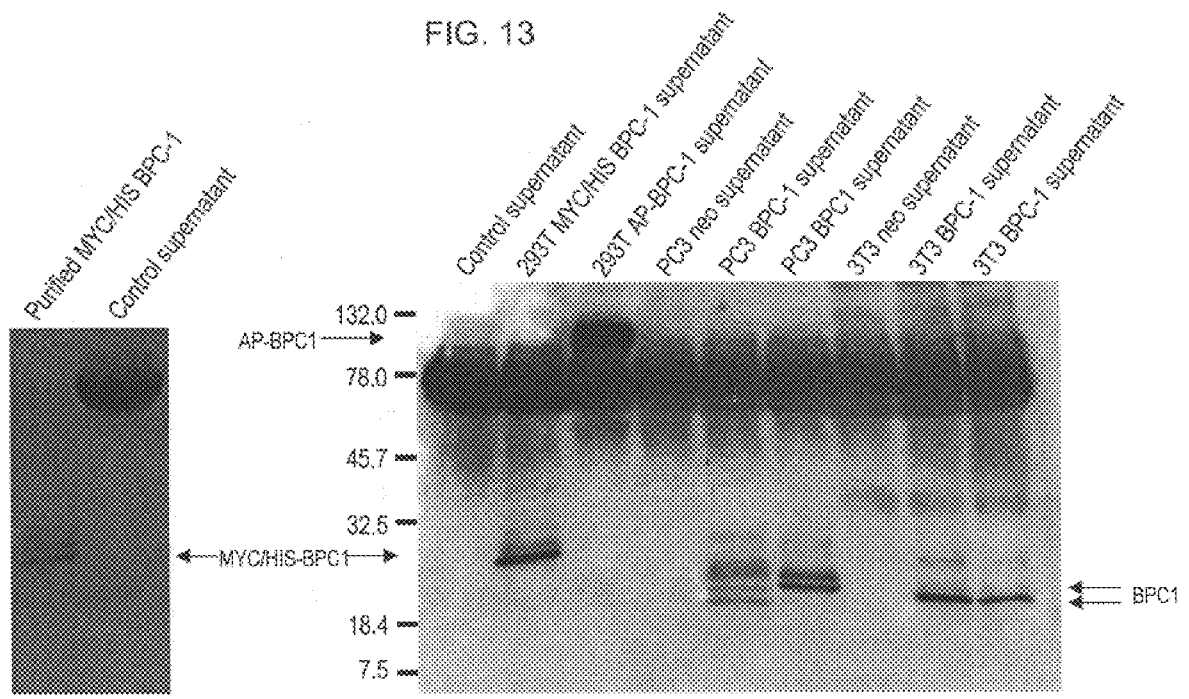
FIG. 13. Western blot detection of BPC-1 protein in tissue culture supernatants of cells expressing the BPC-1 gene. 25 µl of neat supernatant from of various cell lines was subjected to Western blot analysis using a 1:500 dilution of murine anti-BPC-1 polyclonal serum. The blot was then incubated with anti-mouse-HRP conjugated secondary antibody and BPC-1 specific signals were visualized by enhanced chemiluminescent detection. Left blot. Lane 1: Affinity (nickel) purified MYC/HIS BPC-1; Lane 2: 293T control cells, 24 hr conditioned medium. Right blot. Lane 1: 293T control cells, 24 hr conditioned medium; Lane 2: 293T transfected with a MYC/HIS tagged BPC1 vector, 24 hr conditioned medium; Lane 3: 293T cells transfected with an alkaline phosphatase (AP)/BPC-1 fusion vector, 24 hr conditioned medium; Lane 4: PC3 cells infected with control Neo retrovirus and G418 selected, 4 day conditioned medium; Lane 5: PC3 cells infected with BPC-1 retrovirus and G418 selected, 4 day conditioned medium stored 1 week at 4C; Lane 6: PC3 cells infected with BPC-1 retrovirus and G418 selected, 4 day conditioned medium; Lane 7: NIH3T3 cells acutely infected with control Neo retrovirus, 4 day conditioned medium; Lane 8: NIH3T3 cells infected with BPC1 retrovirus and G418 selected, 4 day conditioned medium; Lane 8: NIH3T3 cells acutely infected with BPC1 retrovirus, 4 day conditioned medium.

The mouse polyclonal antibody was successfully used for detecting recombinant BPC-1 expressed in a baculovirus expression system (see Example 7, above), affinity (nickel) purified MYC/HIS BPC-1 protein (FIG. 13) and recombinant BPC-1 protein in tissue culture supernatants of cells expressing the BPC-1 gene (FIG. 13). Rabbit polyclonal serum was also generated and similarly was capable of detecting BPC-1 in tissue culture supernatants of cells expressing the BPC-1 gene.

Example 9

Generation of BPC-1 Monoclonal Antibodies

To generate mAbs to BPC-1, 5 Balb C mice were initially immunized intraperitoneally with 200 μg of GST-BPC-1 fusion protein mixed in complete Freund's adjuvant. Mice were subsequently immunized every 2 weeks with 75 μg of GST-BPC-1 protein mixed in Freund's incomplete adjuvant for a total of 3 immunizations. Reactivity of serum from immunized mice to full length BPC-1 protein was monitored by ELISA using a partially purified preparation of HIS-tagged BPC-1 protein expressed from 293T cells. Two mice with strongest reactivity were rested for 3 weeks and given a final injection of fusion protein in PBS and then sacrificed 4 days later. The spleens of the sacrificed mice were harvested and fused to SPO/2 myeloma cells using standard procedures (Harlow and Lane, 1988). Supernatants from growth wells following HAT selection are being screened by ELISA and Western blot to identify BPC-1 specific antibody producing clones.

The binding affinity of a BPC-1 monoclonal antibody may be determined using standard technology. Affinity measurements quantify the strength of antibody to epitope binding and may be used to help define which BPC-1 monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 10

Production and Purification of Recombinant BPC-1 Expressed in a Mammalian Expression System 293T cells transiently transfected or 293 cells stably expressing a CMV-driven expression vector encoding BPC-1 with a C-terminal 6×His and MYC tag (pcDNA3.1/mycHIS, Invitrogen) serves as source of secreted soluble BPC-1 protein for purification (see Example 6, above). The HIS-tagged BPC-1 protein secreted into the conditioned media is purified using the following method. Conditioned media (500 ml) is concentrated 10 fold and simultaneously buffer exchanged into a phosphate buffer (pH 8.0) containing 750 mM NaCl and 10 mM imidazole using an amicon ultrafiltration unit with a 10 kd MW cutoff membrane. The preparation is then passed over a nickel metal affinity resin with a 0.5 ml bed volume (Ni-NTA, Qiagen) and washed extensively with phosphate buffer (pH 6.0) containing 10% ethanol and 300 mM NaCl. The HIS-tagged BPC-1 protein is then eluted with phosphate buffer (pH 6.0) containing 250 mM imidizole. Higher purity preparations are obtained by repeating the above chromatography step with higher stringency of wash (phosphate buffer containing 75 mM imidizole) or by passage over an anti-HIS Ab immunoaffinity column. This method was successfully used to purify recombinant HIS-BPC-1. A western blot of the purified protein is shown in the far left hand lane of FIG. 13.

Example 11

Retrovirus Mediated Expression of Secreted Human BPC-1

Figure 12:
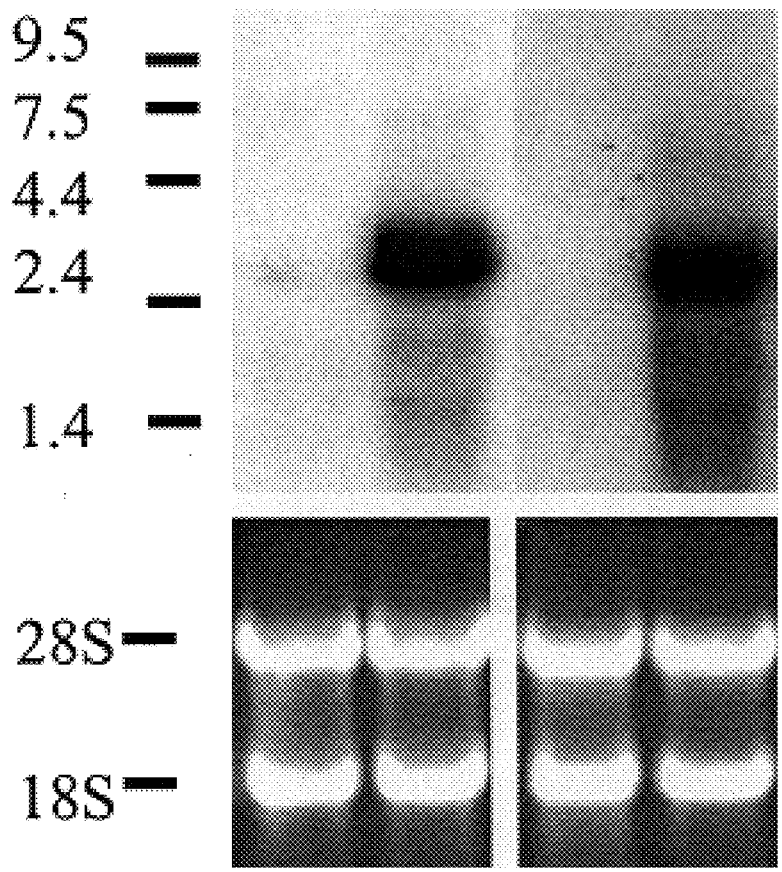
FIG. 12. Northern blot analysis of recombinant human BPC-1 expressed by PC3 and 3T3CL7 cells infected with BPC-1 encoding retrovirus.

The BPC-1 coding region was subcloned into the retroviral SRαmsvtkneo vector (Muller et al., 1991 MCB 11: 1785–1792). Retroviruses were made and used to generate cell lines expressing the BPC-1 gene. The cell lines generated are 3T3/BPC-1 and PC3/BPC-1. 3T3 cells acutely infected with the SR-αBPC-1 virus express a very high level of BPC-1 mRNA, as demonstrated by the Northern blot shown in FIG. 12. The PC3/BPC-1 lysate and supernatant were tested for BPC-1 expression by Western blot analysis using a polyclonal antibody against a GST fusion protein containing the N-terminal portion of the BPC-1 protein (aa29–93) as follows. PC3 and 3T3 cells stably expressing either control(Neo) or BPC-1 encoding retrovirus and 3T3 cells acutely infected with BPC-1 retrovirus were cultured in 10 cm tissue culture plates for 4 days. 25 μl of neat supernatant from each line was subjected to Western blot analysis using a 1:500 dilution of murine anti-BPC-1 polyclonal serum. The blot was then incubated with anti-mouse-HRP conjugated secondary antibody and BPC-1 specific signals were visualized by enhanced chemiluminescent detection. The results of this Western blot analysis are shown in FIG. 13.

Example 12

BPC-1 Expression Analysis in Vitro and in Vivo

Western and immunoprecipitation analyses of cell lysates and conditioned media with BPC-1 specific antibodies may be used to identify and characterize BPC-1 protein expression in cell lines and tissues, such as LAPC4 and LAPC9 xenografts, LNCaP prostate cancer cells, 5637 bladder carcinoma cells, normal human brain lysate, all of which express BPC-1 mRNA, as well as a variety of other carcinoma cell lines, xenografts, and normal tissues. Due to the structural homology of BPC-1 to the porcine and bovine spermadhesin family of proteins (Topfer-Petersen et al. Andrologia, 1998) human semen may also contain detectable levels of BPC-1 protein. Also, given its expression in bladder carcinoma, BPC-1 protein may also be detectable in the urine of bladder carcinoma patients. MYC-HIS BPC-1 transfected 293T cells and retrovirally transduced PC3 and NIH3T3 cells serve as positive controls for BPC-1 protein expression (FIG. 13).

Identification and quantitation of BPC-1 protein present in clinical samples of human serum, semen, and urine may be carried out by capture ELISA as described in the following example. Immunohistochemical analysis of BPC-1 protein in normal and cancerous tissues may be conducted on formalin-fixed, paraffin-embedded or frozen tissue sections using standard immunohistochemical methods well known in the art and the BPC-1 antibodies provided herein. Formalin-fixed, paraffin-embedded sections of LNCaP cells may used as a positive control.

Example 13

BPC-1 Capture ELISA

Capture ELISA may be used to identify and quantify BPC-1 protein present in clinical samples of human serum, semen, and urine as follows. The capture ELISA for BPC-1 is dependent on the generation of at least 2 mAbs of different isotypes that recognize distinct epitopes of the BPC-1 protein or 1 mAb and a specific rabbit polyclonal serum. One reagent will serve as the capture (or coating) Ab and the other as the detection Ab. Captured BPC-1 is then visualized by the addition of a secondary Ab-HRP conjugate against the detection antibody followed by incubation with TMB substrate. Optical density of wells is then measured in a spectrophotometric plate reader at 450 nm. Purified MYC/HIS tagged BPC-1 protein serves as a standardization antigen for the ELISA.

Example 14

BPC-1 Expression Results in Anchorage Independent Colony Formation in Vitro Retrovirally-infected cells expressing BPC-1 were generated as described in EXAMPLE 11 and used along with the respective neo control cell lines to perform soft agar assays to evaluate the oncogenic potential of BPC-1. The agar assay was performed according to conditions previously described (Lugo, T. R and O. N. Witte, 1989, Molec. Cell. Biol. 9: 1263–1270). Briefly, cells were trypsinized and resuspended in Iscove medium containing 0.3% Noble agar and 20% fetal bovine serum. This cell agar suspension ($10^4$ cells/60 mm plate) was plated between a bottom and top layer of medium containing 0.6% Noble agar and 20% fetal bovine serum. The plates were fed after 7 days, and colonies examined and scored 2 or 3 weeks after the agar assay was set up, depending on the size of the colonies. The colonies were counted suing a software from AlphaImager 200. The results are tabulated below in Table 1.

TABLE 1

| BPC-1 EXPRESSION INDUCES CELL TRANSFORMATION | | |
| --- | --- | --- |
| CELLS | AVG. NO. COLONIES [acute infection] | AVG. NO. COLONIES [G418 selection for 2 weeks] |
| 3T3CL7/neo | 14 | 65 |
| 3T3CL7/BPC-1 | 116 | 235 |

3T3CL7 cells infected with retrovirus expressing BPC-1 or neo were used. Colonies were scored 3 weeks after the agar assays were set up. The 3T3CL7/BPC-1 cells generated about 8 fold more colonies compared to the control plate for acutely infected cells. Using G418 selected cells, there are about 3.6 fold more colonies in the 3T3CL7/BPC-1 plates compared to the 3T3CL7/neo plates.

The above results indicate that the BPC-1 protein induces anchorage independent growth in cells experimentally engineered to express and secrete BPC-1 and thus exerts a transforming effect on those cells.

Example 15

BPC-1 Binds to a Cellular Protein

In order to establish whether BPC-1 binds to cellular proteins expressed in prostate cancer cells and other cancer cells or normal cells, two approaches were taken. In the first approach, in vitro assay for recombinant HIS-tagged BPC-1 (Example 6, above) binding to various cell lines are used. In another approach, a recombinant alkaline phosphatase-BPC-1 fusion protein are generated using the AP-TAG system from GenHunter Corporation (Nashville, Tenn., cat# Q202), and the AP-TAG fusion used to test BPC-1 binding to a variety of prostate cancer cell lines.

A. HIS-TAGGED BPC-1 Cell Surface Binding Analysis

PC-3 and NIH3T3 cells are incubated on ice at 4 degrees C for 2 hours with conditioned media containing HIS-tagged BPC-1 (from 293T transfected cells) or media containing purified HIS-tagged BPC-1 or control media. Cells are washed extensively with ice cold PBS with 0.5% FBS and then incubated with an excess of anti-HIS rabbit polyclonal antibody (5 ug/ml, PBS 0.5% FBS) at 4 degrees C for 1 hour. Cells are again washed and then incubated with anti-rabbit FITC conjugated secondary Ab (1:4,000 in PBS/0.5% FBS) for 30 minutes at 4 degrees C. Cell bound BPC-1 is then detected by fluorimetric analysis of cells in a Cytofluor 4000 fluorimeter (PE Biosystems) and/or by flow cytometry.

As an alternative to the fluorescence-based assay used above, binding assays can be carried out with $^{125}$I-labeled BPC-1 protein. Determination of BPC-1 receptor number and affinity on cells and monitoring internalization of receptor bound BPC-1 protein is carried out using standard published procedures (Raitano and Korc, J. Biol. Chem., 1990, J. Biol. Chem. 265: 10466–10472).

B. Alkaline Phosphatase Tagged BPC-1 Generates Cell Surface Staining in Prostate Cancer Cells Alkaline phosphatase-tagged BPC-1 was generated as follows. The sequence encoding mature BPC-1 (i.e., without the signal sequence) was cloned into pAPtag-5 (GenHunter Corp. Nashville, Tenn.). The BPC-1.HindIII and BPC1.BamH1 primers, below, were used to amplify the BPC-1 open reading frame between amino acids 23 and 58 from the plasmid template SRa-19P1E8 clone 1. The HindIII and BamH1 digested PCR product was ligated into HindIII and BglII digested pAPtag-5 while keeping the IgGK signal sequence, BPC-1 ORF, and alkaline phosphatase all in frame. The BPC-1-AP fusion protein contains an IgGK signal sequence to promote secretion along with myc/His tags at the carboxy terminus of alkaline phosphatase.
BPC1.HINDIII PRIMER: (SEQ ID NO. 19)
  GTGTAAGCTTCCACCAAGAAAGGAACAGAA
  (SEQ ID NO. 20)
BPC1.BAMHI PRIMER:
  CACAGGATCCCTTACCAGGTGTGAAATTG To detect whether BPC-1 binds with a cell surface receptor on prostate cancer cells, several prostate cancer cell lines and xenograft tissues are incubated with the BPC-1-AP fusion protein as described (Cheng and Flanagan, 1994, Cell 79:157–168). After washing the cells and adding the AP substrate BCIP, which forms an insoluble blue precipitate upon dephosphorylation, BPC-1 receptor binding is determined by identifying cells staining blue under the light microscope. Various cancer cell lines can be examined, including without limitation, various prostate cancer cell lines (e.g., LNCaP, PC-3, DU145, TSUPR, LAPC4) and bladder carcinoma cell lines. Other cell lines such as PREC prostate cell line, 293T, and NIH 3T3, etc. may also be examined. Additionally, the LAPC and other prostate cancer xenografts may be tested.

Equilibrium dissociation rate constants may be calculated to evaluate the strength of the binding interaction. In addition, the number of cell surface receptors per cell can be determined. Cell lines or tissues with the highest binding capacity for BPC-1 would be preferred for cloning the BPC-1 receptor or other binding partner.

Figure 14:
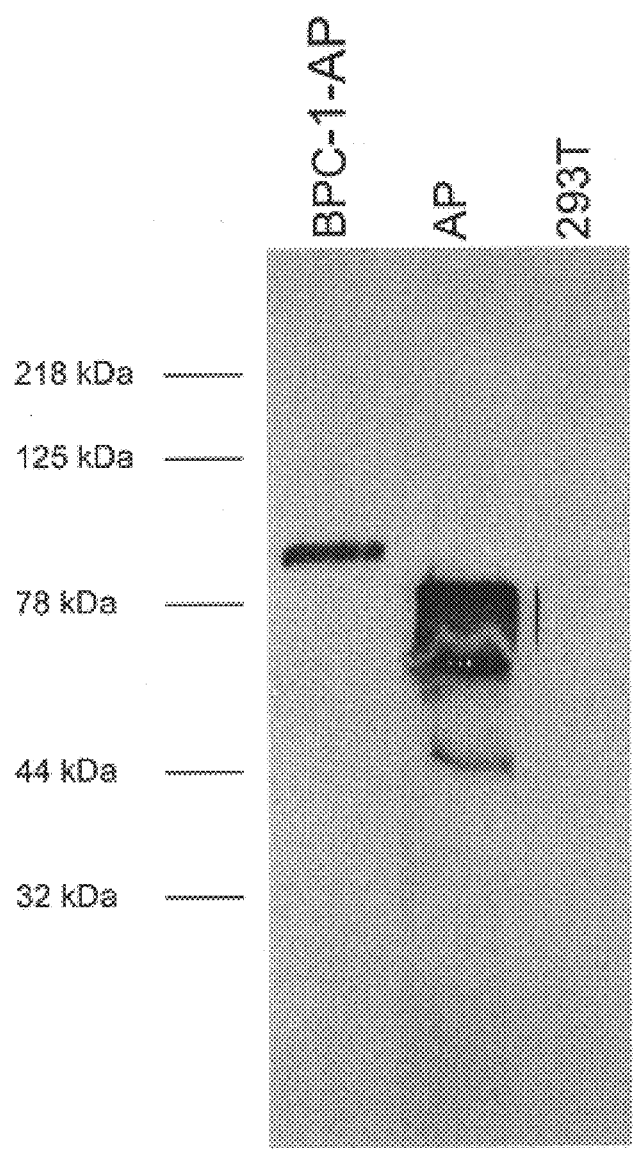
FIG. 14. Western blot analysis showing that BPC-1-AP is present in conditioned media. The lanes contain 20 µl conditioned media from 293T cells or 293T cells collected 48 hours after media change from transfections with the BPC-1-AP construct or with a construct having AP alone. Anti-HIS antibodies were used to detect proteins.

The BPC-1-AP fusion protein was detected in the conditioned media of 293T cells transfected with the above construct by Western blot analysis. Western blot analysis using anti-alkaline phosphatase and anti-HIS antibodies detects the BPC-1-AP fusion protein running at approximately 90 kDa (FIG. 14).

Conditioned media containing this fusion protein was used to detect a 45 kDa binding partner for BPC-1 (FIG. 15), as follows. A western blot procedure was used to identify a 45 kDa receptor interacting with BPC-1. Lysates from brain, testis, prostate, the xenografts LAPC4AD and LAPC9AD, and the cell lines 3T3, LAPC4, LNCaP, and PC-3 were used to generate two duplicate western blots. After blocking in 5% milk in PBS for 1 hr and washing twice with PBS-Tween for 7 minutes each, the blots were incubated with conditioned media from a 293T cell line producing only secreted alkaline phosphatase and with media containing BPC-1-AP fusion protein (see FIG. 14). Following 3 washes with PBS-Tween, the blot was developed using chemiluminescent alkaline phosphatase substrate (Immune-Star, BioRad, cat 170–5010). The results are shown in FIG. 15. The arrow (FIG. 15) shows BPC-1-AP binding to a 45 kDa protein in 3T3, LAPC9AD, LNCaP, PC-3, and to a lesser extent in LAPC4AD and the LAPC-4 cell line. The 45 kDa protein is not detected in brain, testis or prostate. The protein interaction is due to BPC-1 and not AP since the blot shown in FIG. 15 (which was incubated with AP conditioned media) did not detect binding the 45 kDa protein.

Example 16

Identification of Potential Signal Transduction Pathways

To determine whether BPC-1 directly or indirectly activates known signal transduction pathways in cells, luciferase (luc) based transcriptional reporter assays are carried out in cells expressing BPC-1 or exposed to exogenously added BPC-1. These transcriptional reporters contain consensus binding sites for known transcription factors which lie downstream of well characterized signal transduction pathways. The reporters and examples of there associated transcription factors, signal transduction pathways, and activation stimuli are listed below.
1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress Cells to be assayed for BPC-1-mediated effects include LAPC4, LNCaP, PC3, and NIH3T3. The luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 17

In Vitro Assays of BPC-1 Function

A. Cell Invasion/Migration/Chemoattraction Assay

Cell lines expressing BPC-1 may be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and BPC-1 overexpressing PC3, 3T3 and LNCaP cells. To assay whether BPC-1 has chemoattractant properties, parental indicator cells are monitored for passage through the porous membrane toward a gradient of BPC-1 conditioned media compared to control media.

This assay may also be used to qualify and quantify specific neutralization of the BPC-1 induced effect by candidate cancer therapeutic compositions.

B. Cell Growth Assay

To determine whether BPC-1 alters the growth rate of established prostate and non-prostate cell lines, growth curves are generated comparing parental cells transduced with a control retroviral vector to cells transduced with a retrovirus encoding the BPC-1 gene. Cell lines to assay include LNCaP, PC3, TsuPR prostate cell lines and murine NIH3T3 fibroblasts and various other human non-prostate cell lines. In addition, the growth rate of parental cells is assayed in the presence and absence of exogenously added purified MYC-HIS BPC-1. As an alternative source of exogenous BPC-1, conditioned media from the respective BPC-1 retrovirally transduced cell line can be used. Growth of the cell lines is monitored in a 96 well format MTT colorimetric assay (Raitano and Korc, 1990, J. Biol. Chem. 265:10466–10472).

Example 18

In Vivo Models for Studying BPC-1 and Testing Prostate Cancer Therapeutic Compositions

A. Determination of Serum BPC-1 Levels in Mice Bearing Xenogenic Tumors

LNCaP prostate cancer cells and LAPC-4 AD xenograft cells express high levels of BPC-1 as determined by Northern blot analysis. To evaluate BPC-1 as a serum diagnostic marker, SCID mice are injected SQ or orthotopically with either $1\times10^6$ LNCaP or LAPC-4 AD cells. Mice are injected on each flank and tumor growth is monitored by caliper measurements to reflect length×width×height (L×W×H). The mice are bled at the initial appearance of palpable tumors and every week thereafter until tumors are 1,000 mm³ in size. Serial bleeds are screened for the presence of BPC-1 by an ELISA assay as described above. As a control, serum from the tumor-bearing mice is assessed for the secretion of PSA using a specific ELISA kit. To confirm BPC-1 expression, tumors are harvested from the mice and screened for BPC-1 expression by Western blot.

In addition, the 5637 bladder cancer cell line has been shown to express BPC-1 by Northern blot analysis. To evaluate bladder cancer BPC-1 expression, 5637 bladder tumor xenografts are established in SCID mice and serum collected and evaluated for BPC-1 protein by ELISA as described.

Alternatively, prostate cancer cell lines that do not express endogenous BPC-1 and engineered to overexpress BPC-1 may be injected into SCID mice to confirm BPC-1 secretion. These include PC-3, TSUPR1, and DU145. Individual mice are injected SQ with either $1\times10^6$ PC3, TSUPR1, and DU145 cells expressing an empty tkNeo vector (tkNeo) or a vector containing BPC-1. All mice are injected on each flank and tumor growth is monitored by caliper measurements as described above. The mice are bled at the initial appearance of palpable tumors and every week thereafter until tumors are 1,000 mm³ in size. Differences in tumor growth rate, if apparent, are noted and studied further (see below). Serial bleeds may be screened for the presence of BPC-1 by an ELISA assay. To confirm BPC-1 expression, tumors may be harvested from the mice and screened for BPC-1 expression by Western blots.

B. in vivo Assay for BPC-1 Tumor Growth Promotion

The effect of the BPC-1 protein on tumor cell growth may be evaluated in vivo either by gene overexpression or addition of soluble, purified BPC-1 protein to tumor-bearing mice. In the first example, SCID mice are injected SQ on each flank with $1\times10^6$ of either PC3, TSUPR1, or DU145 cells containing tkNeo empty vector or BPC-1. At least two strategies may be used: (1) Constitutive BPC-1 expression under regulation of an LTR promoter, and (2) Regulated expression under control of the ecdysone-inducible vector system. Tumor volume is then monitored at the appearance of palpable tumors and followed over time to determine if BPC-1 expressing cells grow at a faster rate. Additionally, mice may be implanted with $1\times10^5$ of the same cells orthotopically to determine if BPC-1 has an effect on local growth in the prostate or on the ability of the cells to metastasize, specifically to lungs, lymph nodes, and bone marrow.

In the second example, purified BPC-1 protein is be evaluated for an effect on tumor cell growth in vivo. Mice are first divided into groups injected SQ with either $1\times10^6$ LNCaP or LAPC-4 AD cells, which express BPC-1, or PC3 cells, which do not express BPC-1. On the same day as tumor cells are injected, groups are injected IV with a range of purified BPC-1 protein (for example 100, 500, or 1,000 μg). As a control, one group of each tumor type is injected with PBS only. Injections continue 2 times per week for 4 consecutive weeks until tumors grow and reach a size of 1,000 mm³. Tumor volume is followed to determine if BPC-1 has a dose response effect on tumor growth.

In a separate set of experiments to determine if BPC-1 accelerates tumor growth, LNCaP, LAPC-4 AD, and PC3 tumors may be allowed to establish SQ to a size of 100 mm³, at which time purified BPC-1 protein is injected IV in the doses and regimen indicated above. To determine if BPC-1 promotes metastasis, the same tumors may also be implanted orthotopically, and after tumors have been established (determined by circulating PSA levels) purified BPC-1 can be administered as described and metastatic growth evaluated.

The above assays are also useful to determine the BPC-1 inhibitory effect of candidate therapeutic compositions, such as for example, BPC-1 antibodies and intrabodies, BPC-1 mRNA antisense molecules and ribozymes, and BPC-1 receptor compositions.

C. in Vivo BPC-1 Antibody Tumor Inhibition Assay

To study the effect of BPC-1 specific mAbs on the formation and growth of tumors, mice are divided in groups of either BPC-1 positive LNCaP, LAPC-4 AD, and PC3-BPC-1 tumors, or PC3-tkNeo, which does not express BPC-1. To evaluate an effect on tumor formation, mice are injected with $1\times10^6$ tumor cells SQ and on the same day are injected IP with a range of BPC-1 specific mAb or control Ig (for example, 100, 500, or 1,000 μg). Injections of mAbs continue 2 times per week for 4 consecutive weeks. Tumor growth is followed as described above. Alternatively, to evaluate an effect on established tumors, mice are divided into groups bearing established tumors 100 mm³ in size and are injected IP with mAbs according to the doses and regimen described previously. Tumor volume is followed to determine the mAb's effect on growth of established tumors.

To study effect on metastasis, $1\times10^5$ of LAPC-4 AD cells are injected orthotopically into SCID mice. At the same time the mice are injected IP with a range of anti-BPC-1 mAb or control Ig as described above. Tumor growth is followed by weekly determinations of circulating PSA. At the end of the antibody administration, the mice are sacrificed and local tumor growth and metastasis to lungs, lymph nodes, and bone marrow are evaluated. To examine an effect on mice with established tumors, LAPC-4 AD are injected orthotopically and PSA levels are followed weekly. When PSA reaches measurable levels, the mice are injected with the same dose and regimen of mAbs described. The mice are sacrificed after the completion of antibody injections to evaluate local tumor growth as well as metastasis.

Example 19

Molecular Cloning of the BPC-1 Receptor or Binding Partner

Expression cloning strategies such as described in Tartaglia et al., 1995, Cell 83:1263–1271 and Cheng and Flanagan, 1994, Cell 79:157–168 and others may be used to clone the receptor for BPC-1. An expression library is first constructed from cells showing BPC-1-AP binding. The library may be constructed in pools of approximately 1000 clones and then screened by a sib selectil on procedure. Transient transfections of COS cells with DNA from each pool and subsequent screening with BPC-1-AP binding, washing, and staining for AP activity identifies cells binding BPC-1 and consequently expression of BPC-1 receptor. After successive rounds of pool subdivision and screening, single colonies binding to BPC-1-AP can be identified.

An alternative approach to cloning BPC-1 receptor/binding partner genes utilizes expression cloning in phage (Stone J. in Current Protocols in Molecular Biology (1997): 20.3.1–20.3.9). For example, a LAPC-9 AD phage expression library in Lambda Zap Express (Stratagene) may be used. Membrane lifts can be probed using BPC-1-AP and positive clones detected with an alkaline phosphatase chemiluminescent reagent (e.g., BioRad). Plaques binding BPC-1-AP and producing a blue precipitates are selected and plasmids isolated and evaluated for the receptor/binding partner sequences. This approach may also result in the identification of cytoplasmic or secreted proteins interacting with BPC-1.

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. An isolated polynucleotide selected from the group consisting of (a) a polynucleotide having the sequence as shown in FIG. 1 (SEQ ID NO. 1), wherein T can also be U; (b) a polynucleotide having the sequence as shown in FIG. 1 (SEQ ID NO. 1), from nucleotide residue number 793 through nucleotide residue number 1269, wherein T can also be U; (c) a polynucleotide having the sequence as shown in FIG. 1 (SEQ ID NO. 1), from nucleotide residue number 862 through nucleotide residue number 1269, wherein T can also be U (d) a polynucleode encoding a Brain/Prostate cancer CUB protein (BPC-1) polypeptide whose sequence is encoded by the cDNA contained in plasmid p19P1E8 clone 6.1 as deposited with American Type Culture Collection as Accession No. 98833; (e) a polynucleotide encoding an isolated BPC-1 protein having the amino acid sequence as shown in FIG. 1 (SEQ ID NO. 2), from amino acid residue number 1 through amino acid residue number 158; (f) a polynucleotide encoding an isolated BPC-1 protein having the amino acid sequence as shown in FIG. 1 (SEQ ID NO. 2), from amino acid residue number 24 through amino acid residue number 158; and (g) a polynucleotide encoding an isolated BPC-1 protein comprising at least one CUB domain of the BPC-1 protein as shown in FIG. 1 (SEQ ID NO. 2), from about amino acid residue number 51 through about amino acid residue number 158.

2. An isolated polynucleotide comprising the precursor BPC-1 coding sequence as shown in FIG. 1 (SEQ ID NO. 1) from nucleotide residue number 793 through 1269.

3. An isolated polynucleotide comprising the mature BPC-1 coding sequence as shown in FIG. 1 (SEQ ID NO. 1) from nucleotide residue number 862 through 1269.

4. An isolated polynucleotide comprising the BPC-1 CUB domain coding sequence as shown in FIG. 1 (SEQ ID NO. 1) from nucleotide residue number 943 through 1248.

5. An isolated polynucleotide which is fully complementary to a polynucleotide according to claim 1.

6. A recombinant expression vector which contains a polynucleotide according to claim 1.

7. A host cell which contains an expression vector according to claim 6.

8. An isolated polynucleotide according to claim 1 which is labeled with a detectable marker.

9. A process for producing a BPC-1 protein comprising culturing a host cell of claim 7 under conditions sufficient for the production of the polypeptide and recovering the BPC-1 protein from the culture.

10. The process according to claim 9 wherein the BPC-1 protein is secreted into the culture medium.

* * * * *

SEQUENCE LISTING

<160> NUMBER OF SEQ ID NOS: 20

<210> SEQ ID NO 1
<211> LENGTH: 2639
<212> TYPE: DNA
<213> ORGANISM: Homo sapiens

<400> SEQUENCE: 1

```
cagccccggg gcgccggccg cgcgcagcct cgctatccca cccaggctcc gggcttccag      60
gagggtcgcg gagccccaag ccatgactaa ggagcccatt tgatagcaga ggtggcgcgc     120
agcccggcga gccgatgacg gaccccttct tcctgccttc aatgcctcag cggaagatcc     180
ccaagggctg gagcgaggag cgctgccgct ggacatcctc ccggggaggc tgctccgacc     240
tgctgcgcgg cgcgtctgag actggggact gagccactcc gccgccgccg gcgccgccgc     300
cgccgcccgc tccgtcgctg ccgtcggtct ggactggccc ccacctcgct gcgccctctc     360
cccggccccg gccccggctc ggggcgtccc ggggctcgcc ctgcgaccgc cgcctcccgc     420
gcgccgcgtc ctcccgaccc cgcggcggcg acgatgcccg ggaggagggt cctgacggcg     480
gcggcgcgga tggtggcggc cggcgcccgg gtgtgatgcg agcgtcacgg tggggatgct     540
gctggctgcg cggcgctgag ggccagcgag agcgagagcc cgcccggggc ggaggacgga     600
ctcatccgga tctggctgca gcgtgggctc ggagctcccc cttcctctcg gtctccctct     660 cggccccccct ttatttcctt cttgctttgc gtctttaaca cctctcgacc ctgtcctccc     720
cccgccactg gaagtcttcc cgtctctaaa tggaattagt ggagcccgga gcctctggtg     780
taacgcacag acatgatcca tgggcgcagc gtgcttcaca ttgtagcaag tttaatcatc     840
ctccatttgt ctggggcaac caagaaagga acagaaaagc aaaccacctc agaaacacag     900
```

-continued

```
aagtcagtgc agtgtggaac ttggacaaaa catgcagagg gaggtatctt tacctctccc     960
aactatccca gcaagtatcc ccctgaccgg gaatgcatct acatcataga agccgctcca    1020
agacagtgca ttgaacttta ctttgatgaa aagtactcta ttgaaccgtc ttgggagtgc    1080
aaatttgatc atattgaagt tcgagatgga cctttggct tttctccaat aattggacgt     1140
ttctgtggac aacaaaatcc acctgtcata aatccagtg gaagatttct atggattaaa     1200 tttttgctg atggagagct ggaatctatg ggattttcag ctcgatacaa tttcacacct    1260
ggtaagtaag tacttaaaaa aaaaatttct ttttcttcct cattttttcta tcttcatagt    1320 acaaaatctt gtgtaagaca acattatact ttctcagaga atgttccagt tctatttaaa    1380
accaaatcta cagtgctttt tcttttccct acacaaattc tgaaaggaaa agatgttttc    1440
cttaaaacag cctatactag aggtaaagag tagtgactca aggctctaaa tgggcatcag    1500
ccacatcatc aagtggactt tgttatgat ggaatgtgta attggagaga cagtctgtga     1560
taggaaaact atacatagga gctgaataaa cttgaaaaga caattgtagt attataaaat    1620
atatccacca aaatgatctt tggggaactt gaatcaaaag tttatttgtt ctgaaaatta    1680
ccgtgtttca atcaaataga tcctacttta ggaagtagtc tgctctcttt tcaggaaagc    1740
aaattcttaa gagttttgat gaaaggaaaa ctgagacctg taacagccaa atactcattt    1800
acaaggtctt gcagaaattg tgtgcaatta tcaaattatg caatctgtat caattttcct    1860
tttaactcgc tagaattaaa aagatcctgt gttgttgcct ggcccacttg attaagagtt    1920
accattcatt acaataaaaa taggttatca cattttttca ctgcaagaac actacatgca    1980
ttaatttaaa tggaaaaatg attcaaatta cataaagccc attttttata tagtttgttt    2040
tcagtttgta tgtattgttt tatttaagtt aggcaatagc ataatttcaa atatatgtaa    2100
agttggttga agtttgtatt ccatgttaaa gaagtaacat ctaaatacag ctttgatact    2160
cagttaaaaa actaaaattt taaaaattat taatataagt ttaatgatga ctttcattat    2220
gacatcatgg ggtatgttaa atcaagtatt tactgtagca tatatattag ctttaagcat    2280
taggaatgtt tttaataata tcactaaagg attgtggttt taattatgct ttgctgataa    2340
tggattactc acagaaatca tgggtatttc atgtgctaca gtcgaactaa tttgaagtat    2400
tcccaaaagg tacaaatgtt agcttaattt gtttgttcag attattagtg ctagagttgt    2460
aaatggaaag gtaggtattt ttttcttaac tgataatttt gaatataacc tgtacctaga    2520
gacagtgaca tacggcatgt tctaggtttc ataagttata ttttcattct gggtttggtg    2580
atcatgaaaa taatgtcttg gatttaaaat tgtggtttca caaaaaaaaa aaaaaaaa     2639
```

<210> SEQ ID NO 2
<211> LENGTH: 158
<212> TYPE: PRT
<213> ORGANISM: Homo sapiens

<400> SEQUENCE: 2

```
Met Ile His Gly Arg Ser Val Leu His Ile Val Ala Ser Leu Ile Ile
  1               5                  10                  15

Leu His Leu Ser Gly Ala Thr Lys Lys Gly Thr Glu Lys Gln Thr Thr
             20                  25                  30

Ser Glu Thr Gln Lys Ser Val Gln Cys Gly Thr Trp Thr Lys His Ala
         35                  40                  45

Glu Gly Gly Ile Phe Thr Ser Pro Asn Tyr Pro Ser Lys Tyr Pro Pro
     50                  55                  60

Asp Arg Glu Cys Ile Tyr Ile Ile Glu Ala Ala Pro Arg Gln Cys Ile
```

-continued

```
                 65                  70                  75                  80
Glu Leu Tyr Phe Asp Glu Lys Tyr Ser Ile Glu Pro Ser Trp Glu Cys
                         85                  90                  95
Lys Phe Asp His Ile Glu Val Arg Asp Gly Pro Phe Gly Phe Ser Pro
                100                 105                 110
Ile Ile Gly Arg Phe Cys Gly Gln Gln Asn Pro Pro Val Ile Lys Ser
            115                 120                 125
Ser Gly Arg Phe Leu Trp Ile Lys Phe Phe Ala Asp Gly Glu Leu Glu
        130                 135                 140
Ser Met Gly Phe Ser Ala Arg Tyr Asn Phe Thr Pro Gly Lys
145                 150                 155

<210> SEQ ID NO 3
<211> LENGTH: 115
<212> TYPE: PRT
<213> ORGANISM: Caenorhabditis elegans

<400> SEQUENCE: 3

Ile Phe Thr Ser Pro Asn Phe Pro Asp Arg Tyr Pro Pro Asn Ile Asp
  1               5                  10                  15
Cys Val Arg Val Ile His Ser Arg Pro Gln His Asp Val Val Val Lys
                 20                  25                  30
Phe His His Val Phe His Ile Glu Ser Thr Tyr Asp Lys Ile Asp Ala
             35                  40                  45
Gly Glu Glu Cys Pro Asn Asp Phe Ile Glu Phe Arg Asp Gly Arg Tyr
         50                  55                  60
Gly Phe Ser Pro Leu Ile Ala Arg Phe Cys Gly Asp Arg Met Pro Lys
 65                  70                  75                  80
Arg Glu Ile Arg Ala Val Ser Gly Phe Leu Trp Ile Arg Phe Arg Ser
                 85                  90                  95
Asp Ser Met Leu Glu Tyr Gln Gly Phe Ser Ala Glu Tyr Ala Ile Val
            100                 105                 110
Pro Ser Lys
        115

<210> SEQ ID NO 4
<211> LENGTH: 101
<212> TYPE: PRT
<213> ORGANISM: Mouse

<400> SEQUENCE: 4

Gly Asn Phe Ser Ser Pro Glu Tyr Pro Asn Gly Tyr Ser Ala His Met
  1               5                  10                  15
His Cys Val Trp Arg Ile Ser Val Thr Pro Gly Glu Lys Ile Ile Leu
                 20                  25                  30
Asn Phe Thr Ser Met Asp Leu Tyr Arg Ser Arg Leu Cys Trp Tyr Asp
             35                  40                  45
Tyr Val Glu Val Arg Asp Gly Phe Trp Arg Lys Val Trp Val Arg Gly
         50                  55                  60
Arg Phe Cys Gly Gly Lys Leu Pro Glu Pro Ile Val Ser Thr Asp Ser
 65                  70                  75                  80
Arg Leu Trp Val Glu Phe Arg Ser Ser Asn Trp Val Gly Lys Gly
                 85                  90                  95
Phe Phe Ala Val Tyr
            100
```

```
<210> SEQ ID NO 5
<211> LENGTH: 103
<212> TYPE: PRT
<213> ORGANISM: Mouse

<400> SEQUENCE: 5

Asp Asn Gly His Ile Gln Ser Pro Asn Tyr Pro Asp Tyr Arg Pro
 1               5                  10                  15

Ser Lys Val Cys Ile Trp Arg Ile Gln Val Ser Glu Gly Phe His Val
                20                  25                  30

Gly Leu Thr Phe Gln Ser Phe Glu Ile Glu Arg His Asp Ser Cys Ala
            35                  40                  45

Tyr Asp Tyr Leu Glu Val Arg Asp Gly His Ser Glu Ser Ser Asn Leu
     50                  55                  60

Ile Gly Arg Tyr Cys Gly Tyr Glu Asn Pro Asp Asp Ile Lys Ser Thr
65                  70                  75                  80

Ser Ser Arg Leu Trp Leu Lys Phe Val Ser Asp Gly Ser Ile Asn Lys
                85                  90                  95

Ala Gly Phe Ala Val Asn Phe
            100

<210> SEQ ID NO 6
<211> LENGTH: 101
<212> TYPE: PRT
<213> ORGANISM: Mouse

<400> SEQUENCE: 6

Gly Ser Ile Thr Ser Pro Gly Trp Pro Lys Glu Tyr Pro Pro Asn Lys
 1               5                  10                  15

Asn Cys Ile Trp Gln Leu Val Ala Pro Thr Gln Tyr Arg Ile Ser Leu
                20                  25                  30

Gln Phe Asp Phe Phe Glu Thr Glu Gly Asn Asp Val Cys Lys Tyr Asp
            35                  40                  45

Phe Val Glu Val Arg Ser Gly Leu Thr Ala Asp Ser Lys Leu His Gly
     50                  55                  60

Lys Phe Cys Gly Ser Glu Lys Pro Glu Val Ile Thr Ser Gln Tyr Asn
65                  70                  75                  80

Asn Met Arg Val Glu Phe Lys Ser Asp Asn Thr Val Ser Lys Lys Gly
                85                  90                  95

Phe Lys Ala His Phe
            100

<210> SEQ ID NO 7
<211> LENGTH: 102
<212> TYPE: PRT
<213> ORGANISM: Mouse

<400> SEQUENCE: 7

Gly Thr Ile Thr Ser Pro Asn Trp Pro Asp Lys Tyr Pro Ser Lys Lys
 1               5                  10                  15

Glu Cys Thr Trp Ala Ile Ser Ser Thr Pro Gly His Arg Val Lys Leu
                20                  25                  30

Thr Phe Val Glu Met Asp Ile Glu Ser Gln Pro Glu Cys Ala Tyr Asp
            35                  40                  45

His Leu Glu Val Phe Asp Gly Arg Asp Ala Lys Ala Pro Val Leu Gly
     50                  55                  60

Arg Phe Cys Gly Ser Lys Lys Pro Glu Pro Val Leu Ala Thr Gly Asn
65                  70                  75                  80
```

Arg Met Phe Leu Arg Phe Tyr Ser Asp Asn Ser Val Gln Arg Lys Gly
             85                  90                  95

Phe Gln Ala Ser His Ser
            100

<210> SEQ ID NO 8
<211> LENGTH: 95
<212> TYPE: PRT
<213> ORGANISM: Mouse

<400> SEQUENCE: 8

Asn Asn Tyr Pro Gly Gly Val Asp Cys Glu Trp Val Ile Val Ala Glu
 1               5                  10                  15

Glu Gly Tyr Gly Val Glu Leu Val Phe Gln Thr Phe Glu Val Glu Glu
             20                  25                  30

Glu Thr Asp Cys Gly Tyr Asp Tyr Ile Glu Leu Phe Asp Gly Tyr Asp
             35                  40                  45

Ser Thr Ala Pro Arg Leu Gly Arg Tyr Cys Gly Ser Gly Pro Pro Glu
         50                  55                  60

Glu Val Tyr Ser Ala Gly Asp Ser Val Leu Val Lys Phe His Ser Asp
 65                  70                  75                  80

Asp Thr Ile Ser Lys Lys Gly Phe His Leu Arg Tyr Thr Ser Thr
             85                  90                  95

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: cDNA
      synthesis primer

<400> SEQUENCE: 9
ttttgatcaa gctt                                                        14

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: DNA Adaptor
      1

<400> SEQUENCE: 10
ctaatacgac tcactatagg gctcgagcgg ccgcccgggc ag                         42

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: DNA Adaptor
      2

<400> SEQUENCE: 11
gtaatacgac tcactatagg gcagcgtggt cgcggccgag                            40

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: PCR primer

```
                1

<400> SEQUENCE: 12
ctaatacgac tcactatagg gc                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Nested
      primer (NP)1

<400> SEQUENCE: 13
tcgagcggcc gcccgggcag ga                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Nested
      primer (NP)2

<400> SEQUENCE: 14
agcgtggtcg cggccgagga                                                 20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: RT-PCR
      primer

<400> SEQUENCE: 15
tgccgtatgt cactgtctct aggt                                            24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: RT-PCR
      primer

<400> SEQUENCE: 16
gaaatcatgg gtatttcatg tgct                                            24

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: RT-PCR
      primer

<400> SEQUENCE: 17
ttgaattcca agcaaaccac ctcaga                                          26

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: RT-PCR
      primer
```

```
<400> SEQUENCE: 18
aagctcgagt cagacggttc aatagagt                                          28

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: BPC1.
      HINDIII primer

<400> SEQUENCE: 19
gtgtaagctt ccaccaagaa aggaacagaa                                        30

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: BPC1.BAMHI
      primer

<400> SEQUENCE: 20
cacaggatcc cttaccaggt gtgaaattg                                         29
```